(12) United States Patent
McKay et al.

(10) Patent No.: US 9,211,285 B2
(45) Date of Patent: *Dec. 15, 2015

(54) METHODS AND COMPOSITIONS FOR TREATING POST-OPERATIVE PAIN COMPRISING CLONIDINE

(71) Applicants: WARSAW ORTHOPEDIC, INC., Warsaw, IN (US); Medtronic, Inc., Minneapolis, MN (US)

(72) Inventors: William F. McKay, Memphis, TN (US); Amira Wohabrebbi, Memphis, TN (US); Vanja Margareta King, Memphis, TN (US); Phillip Edward McDonald, Plymouth, MN (US); Christopher M. Hobot, Tonka Bay, MN (US); Troy Carter, Hoover, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/097,983

(22) Filed: Dec. 5, 2013

(65) Prior Publication Data

US 2014/0094498 A1 Apr. 3, 2014

Related U.S. Application Data

(63) Continuation of application No. 12/421,144, filed on Apr. 9, 2009, now Pat. No. 8,629,172.

(60) Provisional application No. 61/046,277, filed on Apr. 18, 2008.

(51) Int. Cl.
| | |
|---|---|
| A61K 31/4168 | (2006.01) |
| A61K 9/00 | (2006.01) |
| A61K 9/20 | (2006.01) |
| A61K 31/4162 | (2006.01) |
| A61K 47/34 | (2006.01) |

(52) U.S. Cl.
CPC ............ *A61K 31/4168* (2013.01); *A61K 9/0024* (2013.01); *A61K 9/204* (2013.01); *A61K 31/4162* (2013.01); *A61K 47/34* (2013.01)

(58) Field of Classification Search
CPC .................................................. A61K 31/4168
See application file for complete search history.

(56) References Cited

U.S. PATENT DOCUMENTS

| | | | |
|---|---|---|---|
| 3,190,802 | A | 6/1965 | Zeile at al. |
| 3,020,660 | A | 8/1985 | Zeile et al. |
| 4,624,255 | A | 11/1986 | Schenck et al. |
| 4,765,974 | A | 8/1988 | Tokuda et al. |
| 4,863,457 | A | 9/1989 | Lee |
| 5,175,052 | A | 12/1992 | Tokuda et al. |
| 5,447,947 | A | 9/1995 | Campbell |
| 5,484,607 | A | 1/1996 | Horacek |
| 5,522,844 | A | 6/1996 | Johnson |
| 5,626,838 | A | 5/1997 | Cavanaugh, Jr. |
| 5,635,204 | A | 6/1997 | Gevirtz et al. |
| 5,759,583 | A | 6/1998 | Iwamoto et al. |
| 5,801,188 | A | 9/1998 | Hassenbusch, III et al. |
| 5,868,789 | A | 2/1999 | Huebner |
| 5,869,100 | A | 2/1999 | Horacek |
| 5,942,241 | A | 8/1999 | Chasin et al. |
| 5,942,503 | A | 8/1999 | Jung et al. |
| 5,942,530 | A | 8/1999 | Panetta et al. |
| 5,945,416 | A | 8/1999 | Shannon et al. |
| 5,980,927 | A | 11/1999 | Nelson et al. |
| 6,030,642 | A | 2/2000 | Horacek |
| 6,069,129 | A | 5/2000 | Sandberg et al. |
| 6,147,102 | A | 11/2000 | Borgman |
| 6,179,862 | B1 | 1/2001 | Sawhney |
| 6,248,345 | B1 | 6/2001 | Goldenheim et al. |
| 6,287,588 | B1 | 9/2001 | Shih et al. |
| 6,326,020 | B1 | 12/2001 | Kohane et al. |

(Continued)

FOREIGN PATENT DOCUMENTS

| | | |
|---|---|---|
| WO | 03005961 A2 | 1/2003 |
| WO | 2006011915 A1 | 2/2006 |
| WO | 2006022611 A2 | 3/2006 |
| WO | 2006101540 A1 | 9/2006 |
| WO | 2008014066 A | 1/2008 |
| WO | 2008079868 A1 | 7/2008 |
| WO | 2009100441 A2 | 8/2009 |

OTHER PUBLICATIONS

Marinangeli F, Ciccozzi A, Donatelli F, Di Pietro A, Iovinelli G, Rawal N, Paladini A, Varrassi G. Clonidine for treatment of postoperative pain: a dose-finding study. Eur J Pain. 2002;6(1):35-42.*

(Continued)

*Primary Examiner* — Paul Zarek
(74) *Attorney, Agent, or Firm* — Sorell Lenna & Schmidt LLP

(57) ABSTRACT

The present invention is directed to an implantable drug depot useful for reducing, preventing or treating post-operative pain in a patient in need of such treatment, the implantable drug depot comprising a therapeutically effective amount of clonidine or pharmaceutically acceptable salt thereof and a polymer; wherein the depot is implantable at a site beneath the skin to reduce, prevent or treat post-operative pain, and the depot is capable of releasing (i) about 5% to about 45% of the clonidine or pharmaceutically acceptable salt thereof relative to a total amount of the clonidine or pharmaceutically acceptable salt thereof loaded in the drug depot over a first period of up to 48 hours and (ii) about 55% to about 95% of the clonidine or pharmaceutically acceptable salt thereof relative to a total amount of the clonidine or pharmaceutically acceptable salt thereof loaded in the drug depot over a subsequent period of at least 3 days.

21 Claims, 15 Drawing Sheets

(56) References Cited

U.S. PATENT DOCUMENTS

| | | |
|---|---|---|
| 6,331,311 B1 | 12/2001 | Brodbeck et al. |
| 6,417,184 B1 | 7/2002 | Ockert |
| 6,428,804 B1 | 8/2002 | Suzuki et al. |
| 6,461,631 B1 | 10/2002 | Dunn et al. |
| 6,524,607 B1 | 2/2003 | Goldenheim et al. |
| 6,534,048 B1 | 3/2003 | Borgman |
| 6,534,081 B2 | 3/2003 | Goldenheim et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,756,058 B2 | 6/2004 | Brubaker et al. |
| 6,773,714 B2 | 8/2004 | Dunn et al. |
| 6,921,541 B2 | 7/2005 | Chasin et al. |
| 6,974,462 B2 | 12/2005 | Sater |
| 6,992,110 B2 | 1/2006 | Kranzler et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,345,065 B2 | 3/2008 | Gil et al. |
| 7,361,168 B2 | 4/2008 | Makower et al. |
| 7,367,978 B2 | 5/2008 | Drewry et al. |
| 7,507,398 B2 | 3/2009 | Rabinowitz et al. |
| 7,524,812 B2 | 4/2009 | Ellis et al. |
| 2002/0009454 A1 | 1/2002 | Boone et al. |
| 2002/0058656 A1 | 5/2002 | Ockert |
| 2002/0090398 A1 | 7/2002 | Dunn et al. |
| 2002/0094998 A1 | 7/2002 | Burke et al. |
| 2003/0022926 A1 | 1/2003 | Lavand'Homme |
| 2003/0144570 A1* | 7/2003 | Hunter et al. ............ 600/1 |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0028726 A1 | 2/2004 | Fischer et al. |
| 2004/0072799 A1 | 4/2004 | Li et al. |
| 2004/0082540 A1 | 4/2004 | Hermida Ochoa |
| 2004/0101582 A1 | 5/2004 | Wolicki |
| 2004/0109893 A1 | 6/2004 | Chen et al. |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter et al. |
| 2005/0175709 A1 | 8/2005 | Baty, III et al. |
| 2005/0177135 A1* | 8/2005 | Hildebrand et al. ....... 604/890.1 |
| 2005/0186261 A1 | 8/2005 | Avelar et al. |
| 2005/0197293 A1 | 9/2005 | Mellis et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0091207 A1 | 4/2008 | Truckai et al. |
| 2008/0152709 A1 | 6/2008 | Bortz |
| 2008/0171075 A1 | 7/2008 | Ozturk et al. |

OTHER PUBLICATIONS

Rathmell JP, Lair TR, Nauman B. The role of intrathecal drugs in the treatment of acute pain. Anesth Analg. Nov. 2005;101(5 Suppl):S30-43.*

International Search Report and Written Opinion for Application PCT/US2009/040910 mailed Dec. 11, 2009.

Filos K S et al.: "Hemodynamic and Analgesic Profile After Intrathecal Clonidine in Humans. A Dose-Response Study" Anesthesiology, American Society of Anesthesiologists, Philadelphia, PA, US, vol. 81, Jan. 1, 1994, pp. 591-601, XP000910579, ISSN: 0003-3022 abstract.

ATRIGEL, Drug Delivery Platform, QLT USA, Inc., Revised Jul. 2006, 2 pages.

U.S. Appl. No. 12/056,511, filed Mar. 27, 2008.

U.S. Appl. No. 61/046,269, filed Apr. 18, 2008.

\* cited by examiner

METHODS AND COMPOSITIONS FOR TREATING POST-OPERATIVE PAIN COMPRISING CLONIDINE

This application is a continuation application of co-pending U.S. patent application Ser. No. 12/421,144 filed Apr. 9, 2009 and entitled "Methods and Compositions for Treating Post-Operative Pain Comprising Clonidine", which claims the benefit of the filing date of U.S. Provisional Application No. 61/046,277 filed Apr. 18, 2008 and entitled "Methods and Compositions for Treating Post-Operative Pain Comprising Clonidine". The entire disclosure of these documents are herein incorporated by reference in the present application.

BACKGROUND OF THE INVENTION

Pain relief is of prime importance to anyone treating patients undergoing surgery. Proper pain relief imparts significant physiological and psychological benefits to the patient. Not only does effective pain relief mean a smoother more pleasant post-operative course (e.g., mood, sleep, quality of life, etc.) with earlier discharge from medical/surgical/outpatient facilities, but it may also reduce the onset of chronic pain syndromes (e.g., fibromyalgia, myalgia, etc.).

Pain serves a biological function. It often signals the presence of damage or disease within the body and is often accompanied by inflammation (redness, swelling, and/or burning). In the case of post-operative pain, it may be a result of the surgery, or other treatments such as, for example, management of acute pain following burns or non-surgical trauma. The goal for post-operative pain management is to reduce or eliminate pain and discomfort with medication that cause minimum or no side effects.

The site of the surgery has a profound effect upon the degree of post-operative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to post-operative ileus, nausea, vomiting and urinary retention. These problems are unpleasant for the patient and may prolong hospital stay. Many patients that experience moderate to severe post-operative pain, post-traumatic pain and burning pains, often require pain control at least in the first 3 days after trauma or surgery.

One known class of pharmaceuticals to treat post-operative pain is opioids. This class of compounds is well-recognized as being among the most effective type of drugs for controlling post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Further, because of these side-effects, physicians typically limit the administration of opioids to within the first 24 hours post-surgery. Thus, it would be preferable to use non-narcotic drugs that deliver direct, localized pain control at a surgical site.

One pharmaceutical that is known to the medical profession is clonidine, which is widely recognized as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$) may be represented by the following chemical structure:

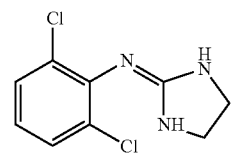

However, to date it has not been widely appreciated as an effective treatment for pain including post-operative pain and/or inflammation. Thus, there is a need to develop effective formulations of this compound for this application.

SUMMARY OF THE INVENTION

New compositions and methods are provided that effectively prevent, treat or reduce post-operative pain or inflammation. In various embodiments, compositions and methods are provided that have long acting analgesic and anti-inflammatory effects over periods of at least 3 days in a single drug depot or multiple drug depots. New compositions and methods are provided, which can easily allow accurate and precise implantation of a drug depot including an antihypertensive agent with minimal physical and psychological trauma to a patient. The drug depot can now be easily delivered to the target tissue site (e.g., abdomen, synovial joint, at or near the spinal column, etc.) and alleviate and/or treat pain for at least 3 to 10 days. In this way, accurate and precise implantation of the drug depot in a minimally invasive procedure can be accomplished.

In one exemplary embodiment, an implantable drug depot useful for reducing, preventing or treating post-operative pain or inflammation in a patient in need of such treatment is provided. The implantable drug depot comprises a therapeutically effective amount of clonidine or pharmaceutically acceptable salt thereof and a polymer. The depot is implantable at a site beneath the skin to reduce, prevent or treat post-operative pain. The depot is capable of releasing (i) about 5% to about 45% of the clonidine or pharmaceutically acceptable salt thereof relative to a total amount of the clonidine or pharmaceutically acceptable salt thereof loaded in the drug depot over a first period of up to 48 hours, a first period of up to 24 hours, or a first period of about 24 to 48 hours and (ii) about 55% to about 95% of the clonidine or pharmaceutically acceptable salt thereof relative to a total amount of the clonidine or pharmaceutically acceptable salt thereof loaded in the drug depot over a subsequent period of at least 3 days, at least 7 days, 3 to 30 days, or 3 to 10 days. The polymer comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof. The polymer may be biodegradeable. In various embodiments, when the first period is up to 24 hours or about 24 to 48 hours, the depot is capable of releasing about 5% to about 30% of the clonidine or pharmaceutically acceptable salt thereof.

In another exemplary embodiment, a method of making an implantable drug depot is provided. The method comprises combining a biocompatible polymer and a therapeutically effective amount of clonidine or pharmaceutically acceptable salt thereof and forming the implantable drug depot from the combination.

In still yet another exemplary embodiment, a method of treating, preventing or reducing post-operative pain in a patient in need of such treatment is provided. The method comprises delivering one or more biodegradable drug depots comprising a therapeutically effective amount of clonidine or pharmaceutically acceptable salt thereof to a target tissue site beneath the skin before, during or after surgery, wherein the drug depot is capable of releasing an initial bolus dose of an effective amount of clonidine or pharmaceutically acceptable salt thereof at a site beneath the skin followed by a sustained release dose of an effective amount of clonidine or pharmaceutically acceptable salt thereof over a period of at least 3 days, at least 7 days, 3 to 30 days, 3 to 10 days, or 5 to 7 days. The drug depot may comprise a polymer and the polymer may comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof. The drug depot is capable of releasing about 40 to 90% of the clonidine or pharmaceutically acceptable salt thereof relative to a total amount of clonidine or pharmaceutically acceptable salt thereof loaded in the drug depot over the sustained release period of 3 to 10 days after the drug depot is administered to the target tissue site. The initial bolus dose of the clonidine may be about 15% to about 45% of the clonidine or pharmaceutically acceptable salt thereof relative to a total amount of clonidine loaded in the drug depot.

In another exemplary embodiment, an implantable drug depot is provided. The implantable drug depot comprises: (i) a therapeutically effective amount of clonidine or pharmaceutically acceptable salt thereof; and (ii) a polymer. The depot is capable of releasing an initial bolus dose of clonidine or pharmaceutically acceptable salt thereof at a site beneath the skin, and the depot is capable of releasing a sustained release dose of an effective amount of clonidine or pharmaceutically acceptable salt thereof over a subsequent period of 3 to 30 days, 3 to 10 days, or 7 to 10 days. The drug depot is capable of releasing about 55% to about 85% of the clonidine or pharmaceutically acceptable salt thereof relative to a total amount of clonidine loaded in the drug depot over the sustained release period of 3 to 30 days, 3 to 10 days, or 7 to 10 days after the drug depot is administered. The polymer comprises one or more of poly(lactide-co-glycolide), polylactide, polyglycolide, polyorthoester, D-lactide, D,L-lactide, poly (D,L-lactide), L-lactide, poly(D,L-lactide-co-caprolactone), poly(D,L-lactide-co-glycolide-co-caprolactone), polycaprolactone or a combination thereof. The initial bolus dose of the clonidine may be about 15% to about 45% of the clonidine or pharmaceutically acceptable salt thereof relative to a total amount of clonidine loaded in the drug depot.

Clonidine in the various embodiments may be in the form of a salt. One example of a salt is a hydrochloric salt. In various embodiments, clonidine may be in the form of a base. Further, clonidine or a pharmaceutically acceptable salt thereof may be encapsulated in a plurality of depots comprising microparticles, microspheres, microcapsules, and/or microfibers which could be suspended in a gel. The drug depot may be a ribbon-like strip. The drug depot can also be a gel formulation.

The polymer in the various embodiments may comprise about 60% to about 90% of the total wt. % of the drug depot. The polymer is capable of degrading or degrades in 30 days or less after the drug depot is implanted at the site. In various embodiments, the polymer may comprise poly(lactic-co-glycolic acid) and the poly(lactic-co-glycolic acid) comprises a mixture of polyglycolide and polylactide. The mixture comprises more polylactide than polyglycolide.

The drug depot in various embodiments may comprise a radiographic marker adapted to assist in radiographic imaging. The radiographic marker may comprise barium, bismuth, tungsten, tantalum, iodine, calcium phosphate, and/or metal beads.

The drug depot in various embodiments may comprise at least one additional anti-inflammatory or analgesic agent, at least one anabolic or an anti-catabolic growth factor or a combination thereof.

The drug depot is capable of releasing between 0.05 microgram (ug) and 3 milligram (mg) per day of clonidine or pharmaceutically acceptable salt thereof to reduce post-operative pain.

The target tissue site comprises at least one muscle, ligament, tendon, cartilage, spinal disc, spinal foraminal space near the spinal nerve root, facet or synovial joint, or spinal canal.

The pain may be associated with surgical amputation, hernia repair, orthopedic or spine surgery or a combination thereof. The surgery may be arthroscopic surgery, an excision of a mass, hernia repair, spinal fusion, thoracic, cervical, or lumbar surgery, an amputation, pelvic surgery or a combination thereof.

One or more drug depots of the present invention may be used to treat conditions of pain and/or inflammation in chronic conditions including rheumatoid arthritis, osteoarthritis, sciatica, carpal tunnel syndrome, lower back pain, lower extremity pain, upper extremity pain, pain associated with an amputation which is sometimes referred to as "phantom pain," cancer, tissue pain and pain associated with injury or repair of cervical, thoracic, and/or lumbar vertebrae or intervertebral discs, rotator cuff, articular joint, TMJ, tendons, ligaments, muscles, or the like.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
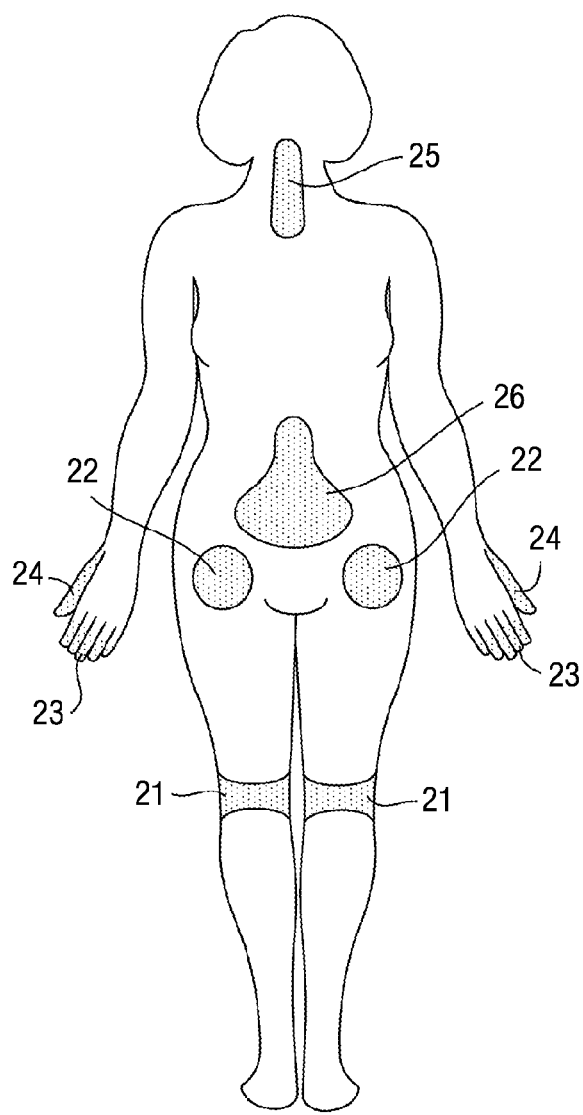
FIG. 1 illustrates a number of common locations within a patient that may be sites where surgery is conducted and locations where the drug depot containing an antihypertensive agent or clonidine can be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New compositions and methods are provided that effectively prevent, treat or reduce post-operative pain or inflammation. In various embodiments, compositions and methods are provided that have long acting analgesic and anti-inflammatory effects over periods of at least 3 days in a single drug depot or multiple drug depots. New compositions and methods are provided, which can easily allow accurate and precise implantation of a drug depot including clonidine with minimal physical and psychological trauma to a patient. The drug depot can now be easily delivered to the target tissue site (e.g., abdomen, synovial joint, at or near the spinal column, etc.) and alleviate and/or treat pain for at least 3 to 10 days. In this way, accurate and precise implantation of the drug depot in a minimally invasive procedure as well as an open procedure can be accomplished.

Clonidine

Clonidine may be contained in a drug depot. A drug depot comprises a physical structure to facilitate implantation and retention in a desired site (e.g., a synovial joint, a disc space, a spinal canal, abdominal area, a tissue of the patient, etc.). The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent for delivery to the site. In various embodiments, the drug depot provides an optimal drug concentration gradient of the therapeutic agent at a distance of up to about 1 cm to about 10 cm from the implant site.

A "therapeutically effective amount" or "effective amount" is such that when administered, the drug results in alteration of the biological activity, such as, for example, inhibition of inflammation, reduction or alleviation of pain, improvement in the condition, etc. In various embodiments, the therapeutically effective amount of clonidine comprises from about 0.1 ug/day to 100 mg/day. In some embodiments, the therapeutically effective amount of clonidine comprises from about 30 ug to 1 mg of clonidine per day. In some embodiments, the therapeutically effective amount of clonidine comprises from about 30 ug to 2.4 mg of clonidine per day. In some embodiments, the therapeutically effective amount of clonidine comprises from about 0.1 mg to 0.3 mg of clonidine per day. In some embodiments, the therapeutically effective amount of clonidine comprises 0.1 ug, 0.2 ug, 0.3 ug, 0.4 ug, 0.5 ug, 0.6 ug, 0.7 ug, 0.8 ug, 0.9 ug, 1 ug, 10 ug, 20 ug, 30 ug, 40 ug, 50 ug, 60 ug, 70 ug, 80 ug, 90 ug, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg (and all ranges and subranges therebetween) of clonidine per day. In one embodiment, the dosage to a human is between 0.1 mg and 0.3 mg of clonidine per day. It will be understood that the dosage administered to a patient can be as single depot or multiple depots depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. For example, lower daily doses of clonidine may be needed when there is concurrent treatment with an opioid (e.g., morphine), alternatively, the patient may require higher doses of clonidine as the dosage of the opioid (e.g., morphine) is reduced or eliminated to control post-operative pain.

In various embodiments, a therapeutically effective amount of clonidine is provided to inhibit, reduce, treat and/or prevent post-operative pain or inflammation. In general, the chemical name of clonidine is 2,6-dichloro-N-2-imidazolidinyldenebenzenamine ($C_9H_9Cl_2N_3$). Clonidine has a molecular weight of 230.09 and exhibits the following general structure:

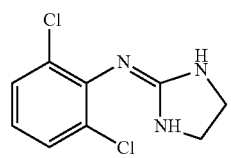 [SMILES: Clc1cccc(Cl)c1N=C1NCCN1]

Unless otherwise specified or apparent from context, where this specification and the set of claims that follows refer to clonidine, it is understood that the inventors are also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non-limiting example, when formulating clonidine with poly(orthoesters), it may be desirable to use the clonidine base formulation. By contrast, when formulating clonidine with PLGA, it may be desirable to use the HCl salt form. In various embodiments, clonidine may be in the form of a combination of a salt and a base.

In addition to clonidine, the drug depot may comprise one or more additional therapeutic agents. Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine Pharma-Sciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dithiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Additional analgesic agents may also be included in the depot. Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Suitable analgesics also include agents with analgesic properties, such as for example, amitriptyline, carbamazepine, gabapentin, pregabalin, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients. These non-active ingredients may have a multi-functional purpose including the carrying, stabilizing and controlling of the release of the therapeutic agent(s). The sustained release process, for example, may be by a solution-diffusion mechanism or it may be governed by an erosion-controlled process. Typically, the depot will be a solid or semi-solid formulation comprised of a biocompatible material, which can be biodegradable. The term "solid" is intended to mean a non-gel like material, while, "semi-solid" is intended to mean a gel-like material that has some degree of flowability, thereby allowing the depot to bend and conform to the surrounding tissue requirements. The term "gel" is intended to mean a material that is soft and deformable at any point in its application to the surgical site.

In various embodiments, the depot material will be durable within the tissue site for a period of time similar to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the predetermined erosion of the depot material can also be used to provide for slow release of the loaded therapeutic agent(s).

In various embodiments, the drug depot may be designed to release the clonidine when certain trigger points are reached (e.g., temperature, pH, etc.) after implantation in vivo. For example, the drug depot may comprise polymers that will release more drug as the body temperature reaches greater than, for example, 102° F., particularly if the drug possesses antipyretic properties. In various embodiments, depending on the site of implantation, the drug depot may release more or less drug as a certain pH is reached. For example, the drug depot may be designed to release the drug as the bodily fluid having a certain pH contact the drug depot (e.g., CSF having a pH of about 7.35 to about 7.70, synovial fluid having a pH of about 7.29 to about 7.45; urine having a pH of about 4.6 to about 8.0, pleural fluids having a pH of about 7.2 to about 7.4, blood having a pH of about 7.35 to about 7.45, etc.).

In various embodiments, the depot may have a high drug loading, such that the clonidine and/or other therapeutic agent comprises about 0.5-90 wt. % of the depot, or 1-50 wt. % of the depot, or 1-25 wt. % of the depot, or 1-10 wt. % of the depot. In various embodiments, the amount of clonidine and/or other therapeutic agent are present in the depot in a range from about 0.1% to about 40% by weight of the depot (including 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.5-5%, 5-10% and 10-20%, etc.).

In various embodiments, the drug depot may release 0.1 ug, 0.2 ug, 0.3 ug, 0.4 ug, 0.5 ug, 0.6 ug, 0.7 ug, 0.8 ug, 0.9 ug, 1 ug, 10 ug, 20 ug, 30 ug, 40 ug, 50 ug, 60 ug, 70 ug, 80 ug, 90 ug, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg, 45 mg, or 50 mg of clonidine per day for a total of at least 3 days, at least 7 days, at least 8 days, 3 to 30 days, 3 to 10 days, 3 to 8 days, 5 to 7 days or 7 to 10 days. In various embodiments, the drug depot may release 0.5 mg to 1 mg of clonidine per hour for a total of at least 3 days, 3 to 10 days, 5 to 7 days or 7 to 10 days to reduce, treat or prevent post-operative pain. In various embodiments, the drug depot releases 5%, 10%, 15%, 20%, 25%, 30%, 35%, 40%, 45%, 50%, 55%, 60%, 65%, 70%, 75%, 80%, 85%, 90%, 95%, or 99% of the clonidine over a period of 3 to 10 days after the drug depot is administered to the target tissue site or 5 to 7 days. The drug depot may have a "release rate profile" that refers to the percentage of active ingredient that is released over fixed units of time, e.g., mg/hr, mg/day, 10% per day for ten days, etc. As persons of ordinary skill know, a release rate profile may be but need not be linear. By way of a non-limiting example, the drug depot may be a strip or a ribbon-like strip or fiber that releases the clonidine over a period of time.

In various embodiments, the drug depot comprises from about 1% to 10% by weight clonidine, 75% to 94% by weight of a polymer and 5% to 15% by weight of an excipient. mPEG may be used as an excipient or plasticizer for a polymer as it imparts malleability to the resulting formulation. PEG 300 may also be used as an excipient. In addition, a combination of PEG 300 and NMP may be used as the excipient.

Exemplary excipients that may be formulated with clonidine in addition to the biodegradable polymer include but are not limited to MgO (e.g., 1 wt. %), 5050 DLG 6E, 5050 DLG 1A, mPEG, TBO-Ac, mPEG, Span-65, Span-85, pluronic F127, TBO-Ac, sorbital, cyclodextrin, maltodextrin and combinations thereof. In some embodiments, the excipient or excipients may comprise from about 0.001 wt. % to about 50 wt. % of the formulation. In some embodiments, the excipient(s) comprise from about 0.001 wt. % to about 40 wt. % of the formulation. In some embodiments, the excipient(s) comprise from about 0.001 wt. % to about 30 wt. % of the formulation. In some embodiments, the excipient(s) comprise from about 0.001 wt. % to about 20 wt. % of the formulation. In some embodiments, the excipient(s) comprise from about 0.5 wt. % to about 20 wt. % of the formulation. In some embodiments, the excipient(s) comprise from about 0.001 wt. % to about 10 wt. % of the formulation. In some embodiments, the excipient(s) comprise from about 0.001 wt. % to about 2 wt. % of the formulation.

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In some instances, it may be desirable to avoid having to remove the drug depot after use. In those instances, the drug depot may comprise a biodegradable material. There are numerous materials available for this purpose and having the characteristic of being able to breakdown or disintegrate over a prolonged period of time when positioned at or near the target tissue. As function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

The drug depot may comprise a polymeric or non-polymeric material as well as a synthetic or naturally occurring material, or a combination thereof. Non-polymeric materials include, for example, cholesterol, stigmasterol, glycerol, estradiol, sucrose, distearate, sorbitan, sorbitan monooleate, sorbitan monopalmitate, sorbitan tristearate, or the like.

In various embodiments, the drug depot comprises a polymer and the polymer will degrade in vivo over a period of less than a year, with at least 50% of the polymer degrading within six months or less. In some embodiments, the polymer is capable of or will degrade in two months, one month or less. In some embodiments, the polymer will degrade significantly within a month, with at least 50% of the polymer degrading into non-toxic residues which are removed by the body, and 100% of the drug being released within a two week period. Polymers should also degrade by hydrolysis by surface erosion, rather than by bulk erosion, so that release is not only sustained but also linear. Polymers which meet this criteria include some of the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid.

A "depot" includes but is not limited to capsules, microspheres, microparticles, microcapsules, microfibers particles, nanospheres, nanoparticles, coating, matrices, wafers, pills, pellets, emulsions, liposomes, micelles, sheets, strips, ribbon-like strips or fibers, mesh, a paste, a slab, pellets, gels, or other pharmaceutical delivery compositions. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, gel, etc.) can break down or degrade within the body to non-toxic components after or while a therapeutic agent has been or is being released. By "bioerodible," it is meant that the depot and/or gel will erode or degrade over time due, at least in part, to contact with substances found in the surrounding tissue, fluids or by cellular action. By "bioabsorbable," it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a bioabsorbable, a bioabsorbable, and/or a biodegradable biopolymer that may provide immediate release, sustained release or controlled release of the drug. Examples of suitable sustained release biopolymers include but are not limited to poly(alpha-hydroxy acids), poly(lactide-co-glycolide) (PLGA or DLG) (which includes poly(lactide-co-glycolide, poly(D-lactide-co-glycolide), poly(L-lactide-co-glycolide) and poly(D,L-lactide-co-glycolide)), polylactide (PLA), poly(D,L-lactide), poly(D-lactide), poly(L-lactide), polyglycolide (PG), polyethylene glycol (PEG), PEG 200, PEG 300, PEG 400, PEG 500, PEG 550, PEG 600, PEG 700, PEG 800, PEG 900, PEG 1000, PEG 1450, PEG 3350, PEG 4500, PEG 8000, conjugates of poly (alpha-hydroxy acids), polyhydroxybutyrate, poly(glycolide-co-trimethylenecarbonate), poly(lactic acid-co-lysine), poly(lactide-co-urethane), poly(ester-co-amide), polyorthoesters (POE), polyaspirins, polyphosphazenes, polyanhydrides; polyketals, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, ε-caprolactone, poly(D,L-lactide-co-caprolactone) (DL-CL or DLCL), poly(D,L-lactide-co-glycolide-co-caprolactone) (DL-G-CL), polycaprolactone (PCL), dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the polymer comprises PLGA or POE or a combination thereof. The PLGA may comprise a mixture of polyglycolide and polylactide and in some embodiments, in the mixture, there is more polylactide than polyglycolide. In some embodiments, the molar ratio of polylactide to polyglycolide is between 50:50 and 100:0. In various embodiments, there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, the polymer comprises DL-CL or a combination thereof. The DL-CL may comprise a mixture of lactide and caprolactone. The molar ratio of lactide to caprolactone can be 10:90 to 90:10 and all subranges therebetween (e.g., 20:80, 30:70, 45:55, 65:35, 67:33, 89:11, etc.).

In some embodiments, the polymer comprises DL-G-CL or a combination thereof. The DL-G-CL may comprise a mixture of lactide, glycolide and caprolactone. In some embodiments, the molar ratio of lactide to glycolide to caprolactone may be 30:20:50. In some embodiments, the mixture may comprise 5-50% lactide, 5-50% glycolide, and 20-80% caprolactone.

In various embodiments, when the drug depot comprises a polymer, it is employed at about 10 wt. % to about 90 wt. %, 10 wt. % to about 50 wt. %, or about 20 wt. % to about 40 wt. % based on the weight of the drug depot.

In some embodiments, at least 75% of the particles have a size from about 1 micrometer to about 200 micrometers. In some embodiments, at least 85% of the particles have a size from about 1 micrometer to about 200 micrometers. In some embodiments, at least 95% of the particles have a size from about 1 micrometer to about 200 micrometers. In some embodiments, all of the particles have a size from about 1 micrometer to about 200 micrometers.

In some embodiments, at least 75% of the particles have a size from about 20 micrometer to about 100 micrometers. In some embodiments, at least 85% of the particles have a size from about 20 micrometers to about 100 micrometers. In some embodiments, at least 95% of the particles have a size from about 20 micrometer to about 100 micrometers. In some embodiments, all of the particles have a size from about 20 micrometer to about 100 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methyl and other paraben, polyvinyl alcohol and phenylethyl alcohol; solubility adjusting agents; stabilizers; and/or cohesion modifiers. Typically, any such inactive materials will be present within the range of 0-75 wt. %, and more typically within the range of 0-30 wt. %. If the depot is to be placed in the spinal area or joint area, in various embodiments, the depot may comprise sterile preservative free material.

The depot can have many different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site.

In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film, strip, ribbon, or sheet, a paste, a slab, microparticles, nanoparticles, pellets, mesh or the like. Flexibility may be a consideration so as to facilitate placement of the drug depot. In various embodiments, the drug depot can be different sizes, for example, the drug depot may be a length of from about 0.5 mm to 100 mm and have a diameter or thickness of from about 0.01 to about 5 mm. In various embodiments, the drug depot may have a layer thickness of from about 0.005 to 5.0 mm, such as, for example, from 0.05 to 2.0 mm. In some embodiments, the shape may be a strip or a ribbon-like strip and the strip or ribbon-like strip has a ratio of width to thickness in the range of 2 to 20 or greater.

Radiographic markers can be included on or in the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, bismuth, iodine, tantalum, tungsten, calcium, and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). In various embodiments, the radiographic marker could be a spherical shape or a ring around the depot.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot will not function as a tissue scaffold and will not allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body. In other embodiments, the drug depot may have pore sizes above 500 microns to allow influx of cells and drug release and the drug depot may function, in this embodiment, as a tissue scaffold.

In one exemplary embodiment, a drug depot for delivering a therapeutic agent to a target tissue site beneath the skin of a patient is provided, the drug depot comprising an effective amount of clonidine, wherein the target tissue site comprises at least one muscle, ligament, tendon, cartilage, spinal disc, spinal foraminal space near the spinal nerve root, facet or synovial joint, or spinal canal.

In various embodiments, the drug depot comprises a gel, which includes a substance having gelatinous, jelly-like, or colloidal properties at room temperature. The gel, in various embodiments, may have the clonidine and optionally one or more additional therapeutic agents dispersed throughout it or suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

When the drug depot is a gel, in contrast to a sprayable gel that typically employs a low viscosity polymer, a gel with a higher viscosity may be desirable for other applications, for example, a gel having a putty-like consistency may be more preferable for bone regeneration applications. In various embodiments, when a polymer is employed in the gel, the polymeric composition includes about 40 wt. % to about 99 wt. % or about 90 wt. % to about 99 wt. % of the gel.

In another exemplary embodiment, the gel is in viscous form is loaded with one or more drug depots (e.g., microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue. In yet another exemplary embodiment, the gel is injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, where after the gel is applied to the target site, it hardens and the drug can be released as the bodily fluid contacts the gel.

In various embodiments, the drug depot is loaded with clonidine and optionally one or more additional therapeutic agents, and delivered to the desired target tissue site (e.g., surgical wound site, inflamed tissue, degenerative tissue, etc.) and, in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., strips, ribbon-like strips, etc.) to begin releasing the therapeutic agent. The strips may be formed from an insoluble or inert substance, but soluble or active once it comes into contact with the target tissue site. Likewise, the drug depot may comprise a substance that dissolves or disperses within the tissue. As the drug depot begins to dissolve within hours to days, the drug depots (e.g., strips) are exposed to body fluids and begin releasing their contents. The drug depot can be formulated to optimize exposure time of the drug depot and release of the therapeutic agent from the drug depot.

In various embodiments, the drug depot (e.g., gel) is flowable and can be injected, sprayed, instilled, and/or dispensed to, on or in the target tissue site. "Flowable" means that the gel formulation is easy to manipulate and may be brushed, sprayed, dripped, painted, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in an osteolytic lesion.

In various embodiments, the drug depot comprises poly (alpha-hydroxy acids), PLGA, PLA, D,L-lactide-glycolide-ε-caprolactone, PG, polyhydroxybutyrate, poly(glycolide-co-trimethylenecarbonate), poly(lactic acid-co-lysine), poly(lactide-co-urethane), poly(ester-co-amide), PEG conjugates of poly (alpha-hydroxy acids), polyorthoesters, polyaspirins, polyphosphazenes, polyanhydrides; polyketals, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, ε-caprolactone, D,L-lactide, D-lactide, L-lactide, D,L-lactide-caprolactone, D,L-lactide-glycolide-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly (d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the drug depot in a controlled and/or sustained manner. For example, the drug depot containing the therapeutic agent and a polymer matrix can be injected at the target tissue site and the polymer matrix breaks down over time (e.g., hours, days) within the target tissue site releasing clonidine and optionally additional therapeutic agents. Thus, the administration of the drug depot can be localized and occur over a period of time (e.g., at least one day to about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80 and 90 days).

The terms "sustained release" or "sustain release" (also referred to as extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in or more of the same depots. In various embodiments, the sustained release and immediate release may be part of separate depots. For example, a bolus or immediate release formulation of clonidine may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot is designed to cause an initial burst dose of therapeutic agent within the first 48 hours or 24 hours after implantation. "Initial burst" or "burst effect" or "bolus dose" refers to the release of therapeutic agent from the drug depot during the first 48 hours or 24 hours after the drug depot comes in contact with an aqueous fluid (e.g., synovial fluid, cerebral spinal fluid, etc.). In some embodiments, the drug depot is designed to avoid this initial burst effect.

In various embodiments, the drug depot contains one or more different release layer(s) that releases a bolus dose of clonidine or pharmaceutically acceptable salt thereof (e.g., 100 ug to 300 ug at a target site beneath the skin) and one or more sustain release layer(s) that releases an effective amount of clonidine or pharmaceutically acceptable salt thereof over a period of 3 to 30 days, 3 to 10 days, or 7 to 10 days. In various embodiments, the one or more immediate release layer(s) comprise PLGA, which degrades faster than the one or more sustain release layer(s), which comprises PLA, which degrades at a slower rate than the PLGA.

In various embodiments, when the drug depot comprises a gel, the gel may have a pre-dosed viscosity in the range of about 1 to about 2,000 centipoise (cps), 1 to about 500 cps, 1 to about 200 cps, or 1 to about 100 cps. After the gel is administered to the target site, the viscosity of the gel will increase and the gel will have a modulus of elasticity (Young's modulus) in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example, when applying the formulation via spray.

In various embodiments, the molecular weight of the gel can be varied by many methods known in the art. The choice of method to vary molecular weight is typically determined by the composition of the gel (e.g., polymer, versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise a material to enhance viscosity and control the release of the drug. Such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises from about 2.5% to 5% by weight clonidine, about 85% to 87.5% by weight PLGA, and about 10% by weight of mPEG.

The drug depot release profile can also be controlled, among other things, by controlling the particle size distribution of the components of the drug depot. In various embodiments, the particle size distribution of the components of the drug depot (e.g., clonidine, gel, etc.) may be in the range of from about 10 μM to 200 μM so that the drug depot can easily be delivered to or at or near the target site by injection, spraying, instilling, etc. In various embodiments, the particle size may be 10 μM, 13 μM, 85 μM, 100 μM, 151 μM, 200 μM and all subranges therebetween.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with clonidine. In one embodiment, the microspheres provide for a sustained release of the clonidine. In yet another embodiment, the gel, which is biodegradable, prevents the microspheres from releasing the clonidine; the microspheres thus do not release the clonidine until they have been released from the gel. For example, a gel may be deployed around a target tissue site (e.g., a nerve root). Dispersed within the gel is a plurality of microspheres that encapsulate the desired therapeutic agent. Certain of these microspheres degrade once released from the gel, thus releasing the clonidine.

Microspheres, much like a fluid, may disperse relatively quickly, depending upon the surrounding tissue type, and hence disperse the clonidine. In some situations, this may be desirable; in others, it may be more desirable to keep the clonidine tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge while the smallest diameter is about 22 gauge. In various embodiments, the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproducing cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot (e.g., ribbon-like strips). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering clonidine into a target tissue site of a patient is provided. The method comprises inserting a cannula or needle at or near a target tissue site and implanting the drug depot containing the clonidine at the target site beneath the skin of the patient. In various embodiments, to administer the drug depot to the desired site, first the cannula or needle can be inserted through the skin and soft tissue down to the target tissue site and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted or injected first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In various embodiments, the drug depot can be sutured to the target site or alternatively the drug depot can be implanted, without suturing. For example, in various embodiments, the drug depot can be a strip-shaped or ribbon-shaped depot and placed at the target site, before, during or after surgery. As another example, the drug depot can be delivered in the form of a gel via a syringe or other injectable delivery directly to the target site, before, during or after surgery.

In various embodiments, when the target tissue site comprises a spinal region, a portion of fluid (e.g., spinal fluid, etc.) can be withdrawn from the target site through a cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of one or more effective dosages of clonidine may be used to prevent, treat or relieve the symptoms of post-operative pain incidental to surgery.

"Localized" delivery includes delivery where one or more drugs are deposited within, at or near a tissue. For example, localized delivery includes delivery to a nerve root of the nervous system or a region of the brain, or in close proximity (within about 10 cm, or preferably within about 5 cm, for example) thereto. "Targeted delivery system" provides delivery of one or more drugs depots (e.g., gels or depot dispersed in the gel, etc.) having a quantity of therapeutic agent that can be deposited at or near the target tissue site as needed for treatment of pain and/or inflammation incidental to surgery.

FIG. 1 illustrates a number of common locations within a patient that may be sites at which surgery took place. It will be recognized that the locations illustrated in FIG. 1 are merely exemplary of the many different locations within a patient that may be at which surgery took place. For example, surgery may be required at a patient's knees 21, hips 22, fingers 23, thumbs 24, neck 25, and spine 26. Thus, during or following these surgeries, the patient may be experiencing post-operative pain and/or inflammation.

The term "pain" includes nociception and the sensation of pain, both of which can be assessed objectively and subjectively, using pain scores and other methods well-known in the art. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, post-operative pain, for example, in the back in the lumbar regions (lower back pain) or in the cervical region (neck pain), leg pain, radicular pain (experienced in the lower back and leg from lumber surgery and in the neck and arm from cervical surgery), abdominal pain from abdominal surgery, and neuropathic pain of the arm, neck, back, lower back, leg, and related pain distributions resulting from disk or spine surgery. Neuropathic pain may include pain arising from surgery to the nerve root, dorsal root ganglion, or peripheral nerve.

In various embodiments, the pain results from "post-surgical pain" or "post-operative pain" or "surgery-induced pain", which are used herein interchangeably, and refer to pain arising in the recovery period of seconds, minutes, hours, days or weeks following a surgical procedure (e.g., hernia repair, orthopedic or spine surgery, etc.). Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery or a combination thereof.

The term "pain management medication" includes one or more therapeutic agents that are administered to reduce, prevent, alleviate or remove pain entirely. These include anti-inflammatory agents, muscle relaxants, analgesics, anesthetics, narcotics, etc., or combinations thereof.

In various embodiments, the post-surgical pain or post-operative pain or surgery-induced pain, is accompanied by inflammation. Inflammation can be an acute response to trauma or surgery. When tissues are damaged, TNF-α attaches to cells to cause them to release other cytokines that cause inflammation. The purpose of the inflammatory cascade is to promote healing of the damaged tissue, but once the tissue is healed the inflammatory process does not necessarily end. Left unchecked, this can lead to degradation of surrounding tissues and associated pain. Thus, pain can become a disease state in itself. That is, when this pathway is activated, inflammation and pain ensue. Often a vicious and seemingly endless cycle of insult, inflammation, and pain sets in.

Figure 2:
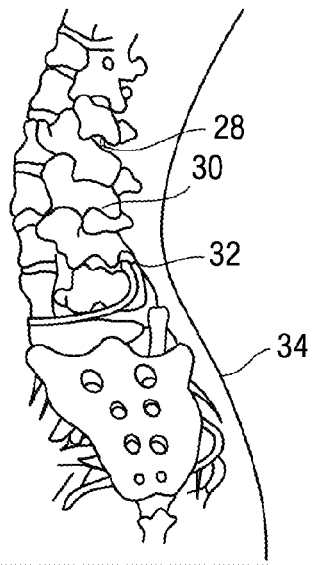
FIG. 2 illustrates a schematic dorsal view of the spine and sites where a drug depot containing an antihypertensive agent or clonidine can be administered thereto.

One exemplary embodiment where the depot is suitable for use in pain and/or inflammation management (e.g., post-operative pain and/or inflammation management) is illustrated in FIG. 2. Schematically shown in FIG. 2 is a dorsal view of the spine and sites where the drug depot may be inserted using a syringe, cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. In various embodiments, the drug depot containing clonidine can be administered to the patient intra-operatively, intravenously, intramuscularly, continuous or intermittent infusion, intraperitoneal, intrasternal, subcutaneously, intrathecally, intradiskally, peridiskally, epidurally, perispinally, intraarticular injection, parenterally, or via combinations thereof. In some embodiments, the injection is intrathecal, which refers to an injection into the spinal canal (intrathecal space surrounding the spinal cord). An injection may also be into a muscle or other tissue.

In some embodiments, it is preferable to co-administer clonidine with an antagonist to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included.

These compounds may prevent or reduce glial and fibroblastic scar formation associated with some types of surgeries.

The clonidine-based formulations of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the statin per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

In various embodiments, where the target tissue site comprises blood vessels, a vasoconstrictor may be employed in the drug depot. When the vasoconstrictor is released, it lengthens the duration of the analgesic response and reduces the systemic uptake of the agent. The analgesic may be, for example, clonidine, and the vasoconstrictor may be, for example, epinephrine or phenylephrine.

The term "patient" refers to organisms from the taxonomy class "mammalian," including but not limited to humans, other primates such as chimpanzees, apes orangutans and monkeys, rats, mice, cats, dogs, cows, horses, etc.

Method of Making Clonidine Depots

In various embodiments, the drug depot comprising the clonidine can be made by combining a biocompatible polymer and a therapeutically effective amount of clonidine or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise one or more of the following: clonidine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding the biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is pre-compounded with a radiographic agent (e.g., radio-opacifying agent) under conditions of temperature and mechanical shear that would result in substantial degradation of the therapeutic agent, if it were present. This pre-compounded material is then mixed with therapeutic agent under conditions of lower temperature and mechanical shear, and the resulting mixture is shaped into the clonidine containing drug depot. Conversely, in another embodiment, the biocompatible polymer can be pre-compounded with the therapeutic agent under conditions of reduced temperature and mechanical shear. This pre-compounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear, in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of clonidine, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where the therapeutic agent is water-soluble, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, clonidine is used and mixed or sprayed with PLGA, poly(D, L-lactide-co-caprolactone) polymer, and/or poly(D,L-lactide-co-glycolide-co-caprolactone) polymer and the resulting depot may be formed by extrusion and dried.

In an exemplary formulation, there is 0.1-10% clonidine, 75-94% PLGA and 5-15% mPEG. Some of these formulations will release between 10 and 30% of the active ingredient on day 1 and all or substantially all of the active ingredient by day 10. Some of these formulations will release between 15 and 25% of the active ingredient on day 1 and all or substantially all of the product by day 10.

In another exemplary embodiment, an implantable drug depot useful for reducing, preventing or treating post-operative pain in a patient in need of such treatment is provided. The implantable drug depot comprises a therapeutically effective amount of clonidine or pharmaceutically acceptable salt thereof and the depot is implantable at a site beneath the skin to reduce, prevent or treat post-operative pain. The drug depot comprises (i) one or more immediate release layer(s) that is capable of releasing about 15% to about 45% of the clonidine or pharmaceutically acceptable salt thereof relative to a total amount of the clonidine or pharmaceutically acceptable salt thereof loaded in the drug depot over a first period of up to 48 hours and (ii) one or more sustain release layer(s) that is capable of releasing about 55% to about 85% of the clonidine or pharmaceutically acceptable salt thereof relative to a total amount of the clonidine or pharmaceutically acceptable salt thereof loaded in the drug depot over a subsequent period of up to 4 to 10 days.

In yet another exemplary embodiment, an implantable drug depot is provided in which the depot comprises: (i) a therapeutically effective amount of clonidine or pharmaceutically acceptable salt thereof; (ii) one or more immediate release layer(s) that is capable of releasing a bolus dose of clonidine or pharmaceutically acceptable salt thereof at a site beneath the skin; and (iii) one or more sustain release layer(s) that is capable of releasing an effective amount of clonidine or pharmaceutically acceptable salt thereof over a period of 4 to 10 days. The one or more immediate release layer(s) comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof, and the one or more sustain release layer(s) comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

Having now generally described the invention, the same may be more readily understood through the following reference to the following examples, which are provided by way of illustration and are not intended to limit the present invention unless specified.

EXAMPLES

Example 1

Implants comprising clonidine were prepared according to the following procedures:

Materials: Poly(D,L-lactide-co-glycolide) having a 50:50 lactide to glycolide molar ratio (PLGA50501A), a molecular weight of 8 kDa, an intrinsic viscosity of 0.12 dL/g and acid end capped polymer chain ends was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol and acetone were also purchased from Sigma-Aldrich.

Methods:

Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for an additional 24 hours at 70° C. and 15 mmHg vacuum.

Preparation of Melt Extruded Rods: Two formulations were prepared for melt extrusion. Both formulations contained PLGA50501A ground into powder using a Retsch (Retsch GmbH, Germany) rotor mill with an 80 micrometer sieve filter. The first such formulation contained 85% (w/w) ground PLGA50501A, 5% (w/w) spray-dried clonidine HCl, and 10% (w/w) mPEG. The second formulation contained 87.5% (w/w) ground PLGA50501A, 2.5% (w/w) spray-dried clonidine HCl, and 10% (w/w) mPEG. Both formulations were dry mixed with a spatula prior to being fed into a Haake Mini-Lab twin screw extruder (Thermo Fischer Scientific, Waltham, Mass.). The extruder settings were as follows: 70° C. and 30 RPM for the 2.5% and 5% clonidine formulations. Both formulations were extruded out of a 1.5 mm diameter dye.

Strip Preparation: Extruded formulations were pressed into sheets of a desired thickness using a Carver Laboratory Heat Press (Carver, Inc., Wabash, Ind.) set at 50° C. The sheets were cut by razor blades to form strips or ribbons of the desired dimensions. The dimensions of the strips or ribbons were as follows (L×W×H which is length by width by height): the strips or ribbons comprising the 2.5% clonidine formulation were 9 mm×1.5 mm×0.5 mm, and the strips or ribbons comprising the 5.0% clonidine formulation were 9 mm×1.5 mm×0.5 mm. It should be noted that the size of the strips or ribbons was selected for a rat paw implant.

Figure 3:
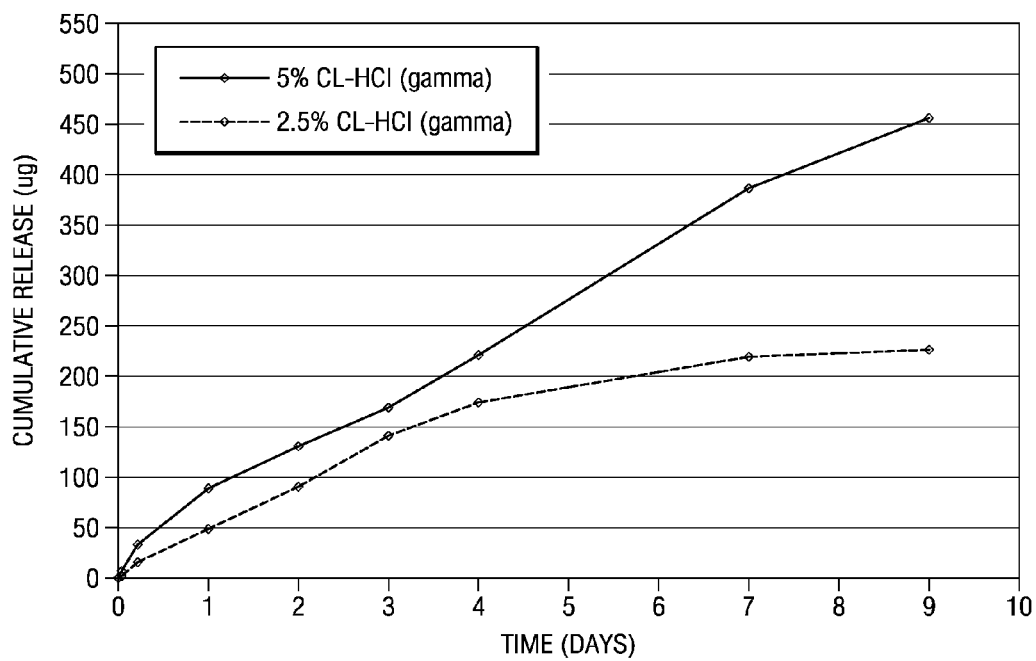
FIG. 3 is a graphic representation of a study of the average cumulative release in ug of clonidine for clonidine strip implants described in Example 1.
Figure 4:
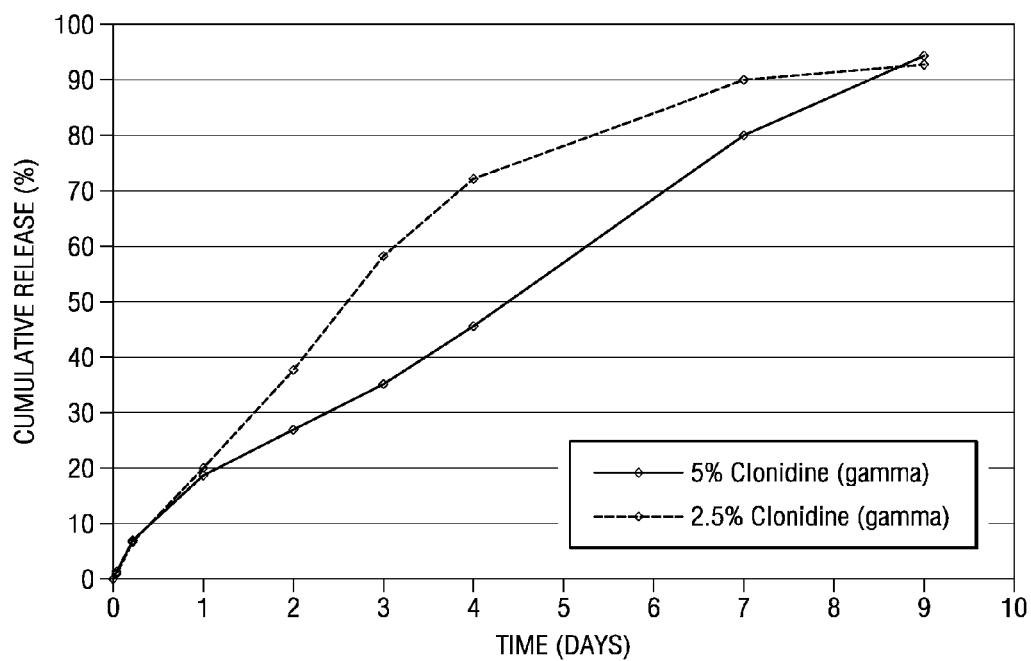
FIG. 4 is a graphic representation of a study of the average percentage cumulative release of clonidine for clonidine strip implants described in Example 1.

In Vitro Drug Elution Testing: Each strip or ribbon implant was tested in triplicate and placed in 20 mL scintillation vials for drug elution testing. The 5% clonidine and 2.5% clonidine strips or ribbons were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. FIGS. 3 and 4 show the average release rate of clonidine in micrograms and percentages for strip or ribbon implants. In particular, in FIG. 3, the 5% clonidine strips released faster (over 450 mcg in 9 days) than the 2.5% clonidine strips (over 200 mcg over 9 days). From FIG. 3, it is apparent that the more wt. % drug load, the greater the release of drug. In FIG. 4, the 2.5% clonidine strips released faster than the 5% clonidine strips, however, the 5% clonidine strips had a steadier release than the 2.5% clonidine strips. Table 1 below summarizes the elution profile for the 5% clonidine and 2.5% clonidine strips.

In vivo data: These implants of clonidine were tested in Brennan rats to determine their in vivo performance. The results are summarized below in Table 1:

TABLE 1

| Implant Number | Polymer (wt. %) | Active wt. % of Clonidine | Excipient (wt. %) | Handling Property | In vitro elution profile | In vivo data |
| --- | --- | --- | --- | --- | --- | --- |
| clonidine 1 | 85% PLGA 5050 1A | 5% (clonidine HCl) | 10% mPEG | Malleable | Day 1 release of 18%; by Day 9, 100% release | Statistically significant reduction in mechanical hyperalgesia on Days 2 and 3 |
| clonidine 2 | 85% PLGA 5050 1A | 2.5% (clonidine HCl) | 10% mPEG | Malleable | Day 1 release of 22%; by Day 9, 100% release | Statistically significant reduction in mechanical hyperalgesia on Days 2-4 |

Figure 5:
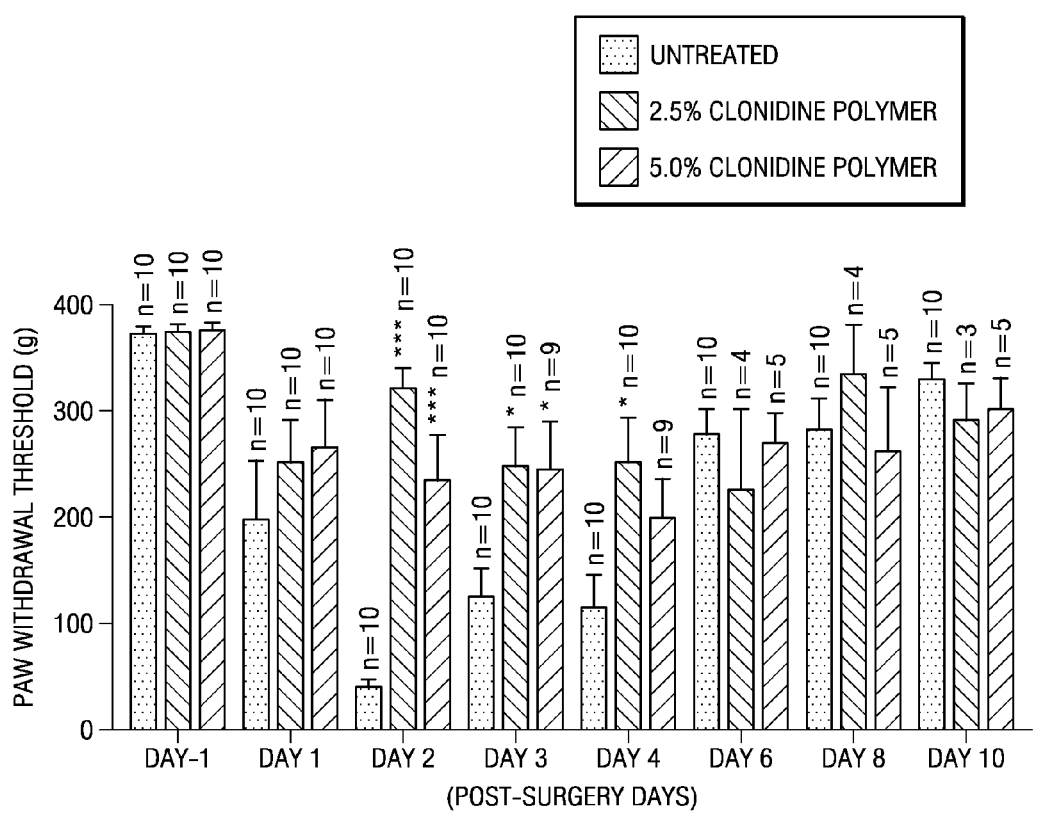
FIG. 5 is a graphic representation of the thermal paw withdrawal threshold in grams per days post-surgery for clonidine implants from Example 1.

For all of the clonidine 1 and 2 implants, the polymer degraded in less than one month and the handling was of a malleable and formable product that could be extruded to a strip or ribbon-like dosage form. The efficacy of the clonidine 1 and 2 implant formulations was tested in the Brennan rat model of post-incisional pain. Mechanical hyperalgesia was used as the behavioral endpoint to assess the presence/absence of pain in the animal model following treatment with these drug formulations. Clonidine 1 implants showed statistically significant reduction in mechanical hyperalgesia on days 2 and 3 following administration compared to Brennan rats receiving no treatment. Clonidine 2 implants, though, showed statistical reversal in mechanical hyperlagesia on days 2, 3, and 4. This preliminary in vivo study has demonstrated both clonidine 1 and 2 implant formulations are effective in treating post-incisional pain in the Brennan rat as assessed by rats' behavioral response to mechanical stimuli following treatment with the clonidine implants. FIG. 5 shows the thermal paw withdrawal threshold in grams per day post-surgery (as measured at day −1, day 1, day 2, day 3, day 4, day 6, day 8 and day 10 post-surgery) for the clonidine 1 and 2 implants. In FIG. 5, "n" represents the number of animals. These measurements are indicative of mechanical hyperalgesia in clonidine treated animals. Starting two days after the depot was implanted, there was a significant decrease in pain (indicated by the *).

Example 2

A number of strip or ribbon implants comprising clonidine were prepared in which the polymer type, drug load, and excipient (including some formulations in which there was no excipient) were varied. Representative formulations for the strip or ribbon implants are described below in Table 2. A number of tests were performed on these strip or ribbon implants, including in vitro release tests in which the number of micrograms released was measured, as well as the cumulative percentage release of clonidine. The results of these tests appear in FIGS. 6-13.

lar weight of 51 kDa, an inherent viscosity of 0.4 dL/g and acid end capped polymer chain ends (6535 DLCL 4A) was purchased from Lakeshore Biomaterials (Birmingham, Ala.). Poly(D,L-lactide-co-caprolactone) having a 25:75 lactide to caprolactone molar ratio, a molecular weight of 62 kDa, an inherent viscosity of 0.5 dL/g and acid end capped polymer chain ends (2575 DLCL 5A) was purchased from Lakeshore Biomaterials (Birmingham, Ala.). Clonidine HCl was purchased from Spectrum Chemicals (Gardena, Calif.). Pluronic F127 which is a nonionic surfactant, polyoxyethylene polyoxypropylene block copolymer (also known as Poloxamer 407) was purchased from BASF. Methanol and acetone were also purchased from Sigma-Aldrich.

Method of Preparation of Strip Implants: Several formulations were made according to the following method and the composition of these formulations is provided in Table 2 below associated with a batch number. For each formulation, the polymer, clonidine, and excipient (where included) were weighed into a glass lyophilization bottle. Glacial acetic acid was added to the bottle and sonicated for approximately 45 minutes to dissolve all of the components (approximately 5 grams of solids per 80 mL of acetic acid). The solution was then shell-frozen in an isopropyl alcohol/dry ice bath. The frozen material was then lyophilized for 24-72 hours to remove the glacial acetic acid. The resulting bulk material intermediate was then pressed into a thin film or sheet using a Carver Laboratory Heat Press (Carver, Inc., Wabash, Ind.). The film or sheet was prepared using a 0.25 mm shim at 65° C. and pressed for 1 minute at 5000 psi pressure. The sheet for each formulation was cut by razor blades to form strips or ribbons of a desired dimension. The dimensions of all of the strips or ribbons was 10 mm in length by 2 mm in width by 0.4 mm thick which was sized for a rat paw. The composition of the formulation used to make strips or ribbons is provided below in Table 2 associated with a batch number and the average amount of clonidine released daily by strips or ribbons made from each formulation is provided in Table 2 below.

TABLE 2

| Batch Number for Strips or Ribbons | Clonidine (wt. %) | 5050 DLG 2A (wt. %) | 1090 DL-CL 10A (wt. %) | 6535 DL-CL 4A (wt. %) | 2575 DL-CL 5A (wt. %) | Excipient (Pluronic F127) (wt. %) | Amount of Release of Clonidine for Day 1 (ug) | Amount of Daily Release of Clonidine for Days 2-10 (ug) |
|---|---|---|---|---|---|---|---|---|
| 00268-15 | 5 | — | 95 | — | — | — | 60 | 30-80 |
| 00268-22 | 5 | 15 | — | 75 | — | 5 | 25 | 10-80 |
| 00268-23 | 5 | 15 | — | — | 75 | 5 | 130 | 40-5 |
| 00268-24 | 2.5 | 16 | — | 38 | 38 | 5 | 35 | 30-50 |
| 00268-31 | 5 | — | 47.5 | 47.5 | — | — | 45 | 15-20 |
| 00268-32 | 5 | 25 | — | 60 | — | 5 | 30 | 20-70 |
| 00268-33 | 7 | 14.7 | — | 73.4 | — | 4.9 | 40 | 120-50 |
| 00268-34 | 5 | 15 | — | 60 | 20 | — | 15 | 5-20 |
| 00268-35 | 1 | 20 | — | 37.1 | 37.1 | 4.8 | 10 | 10-20 |
| 00268-36 | 2.5 | 25.5 | — | 33.5 | 33.5 | 5 | 25 | 20-40 |

Materials: Poly(D,L-lactide-co-glycolide) having a 50:50 lactide to glycolide molar ratio having a molecular weight of 18 kDa, an inherent viscosity of 0.2 dL/g and acid end capped polymer chain ends (5050DLG 2A) was purchased from Lakeshore Biomaterials (Birmingham, Ala.). Poly(D,L-lactide-co-caprolactone) having a 10:90 lactide to caprolactone molar ratio, a molecular weight of 149 kDa, an inherent viscosity of 1.0 dL/g and acid end capped polymer chain ends (1090 DLCL 10A) was purchased from Lakeshore Biomaterials (Birmingham, Ala.). Poly(D,L-lactide-co-caprolactone) having a 65:35 lactide to caprolactone molar ratio, a molecu- The handling properties of strips or ribbons from the batch numbers identified in Table 2 were noted. In particular, the strips or ribbons of batch numbers 00268-15, 00268-22, 00268-23 and 00268-24 were all found to be very flexible. Strips of batch number 00268-15 were firm, strips of batch number 00268-22 were soft and strips of batch numbers 00268-23 and 00268-24 were sticky. The strips of batch numbers 00268-31, 00268-32, 00268-33, 00268-34 and 00268-35 were all found to be very flexible.

Figure 6:
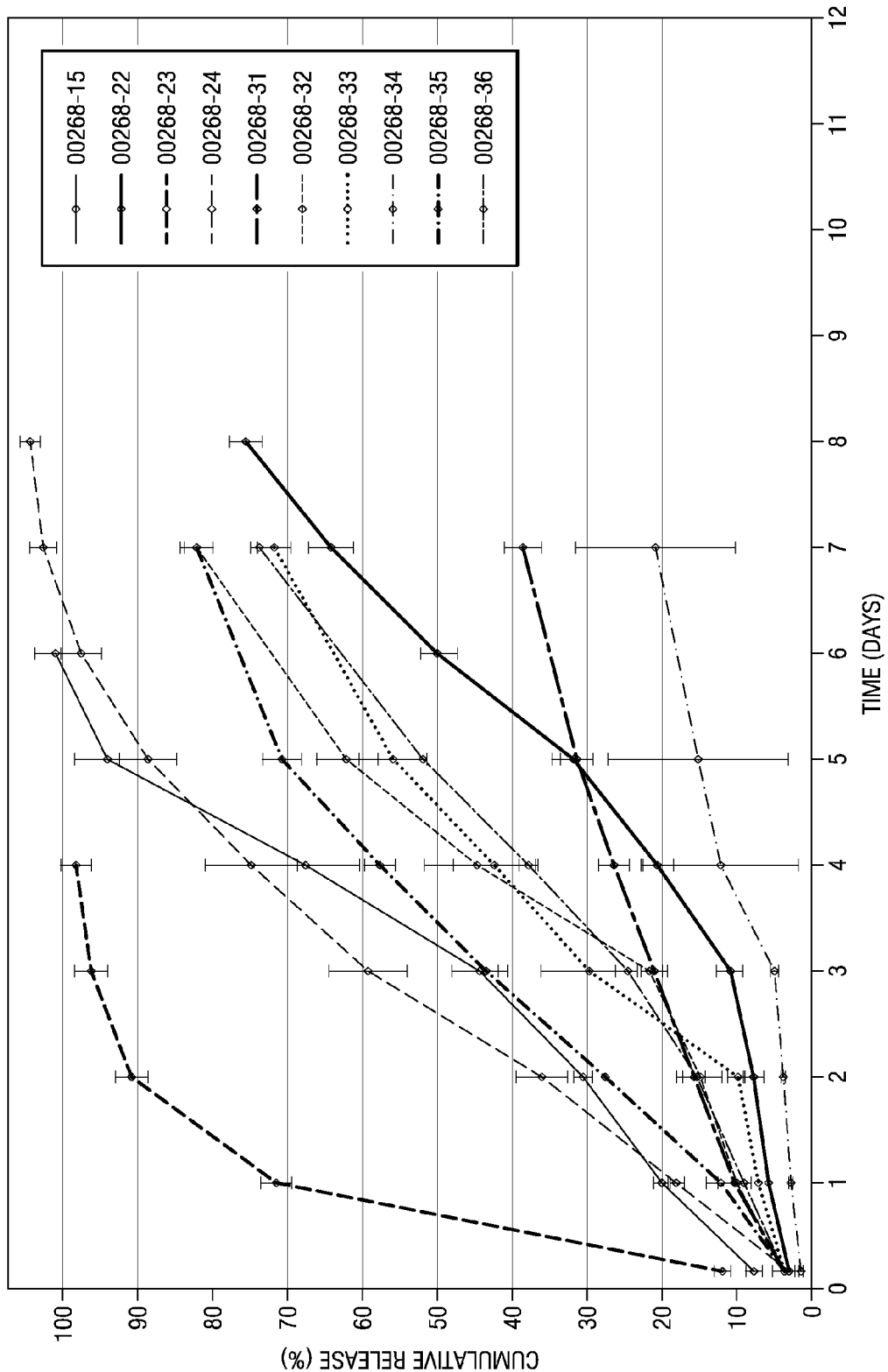
FIG. 6 is a graphic representation of the average percentage cumulative release of clonidine for several irradiated clonidine HCl strip or ribbon implants from Example 2 during days 1-8.
Figure 7:
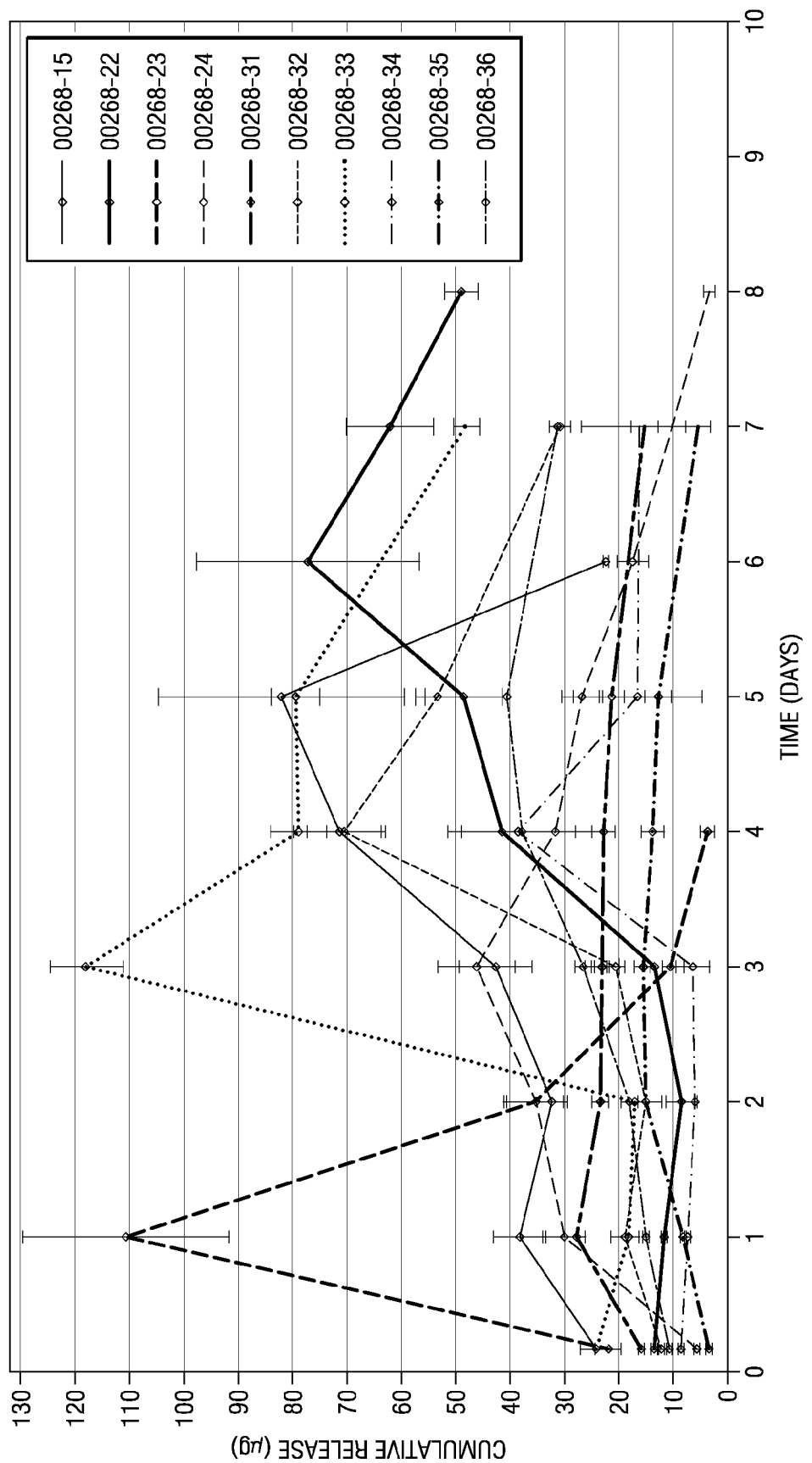
FIG. 7 is a graphic representation of the calculated average daily release of clonidine in micrograms during days 1-8 for the clonidine HCl strip or ribbon implants from Example 2.
Figure 8:
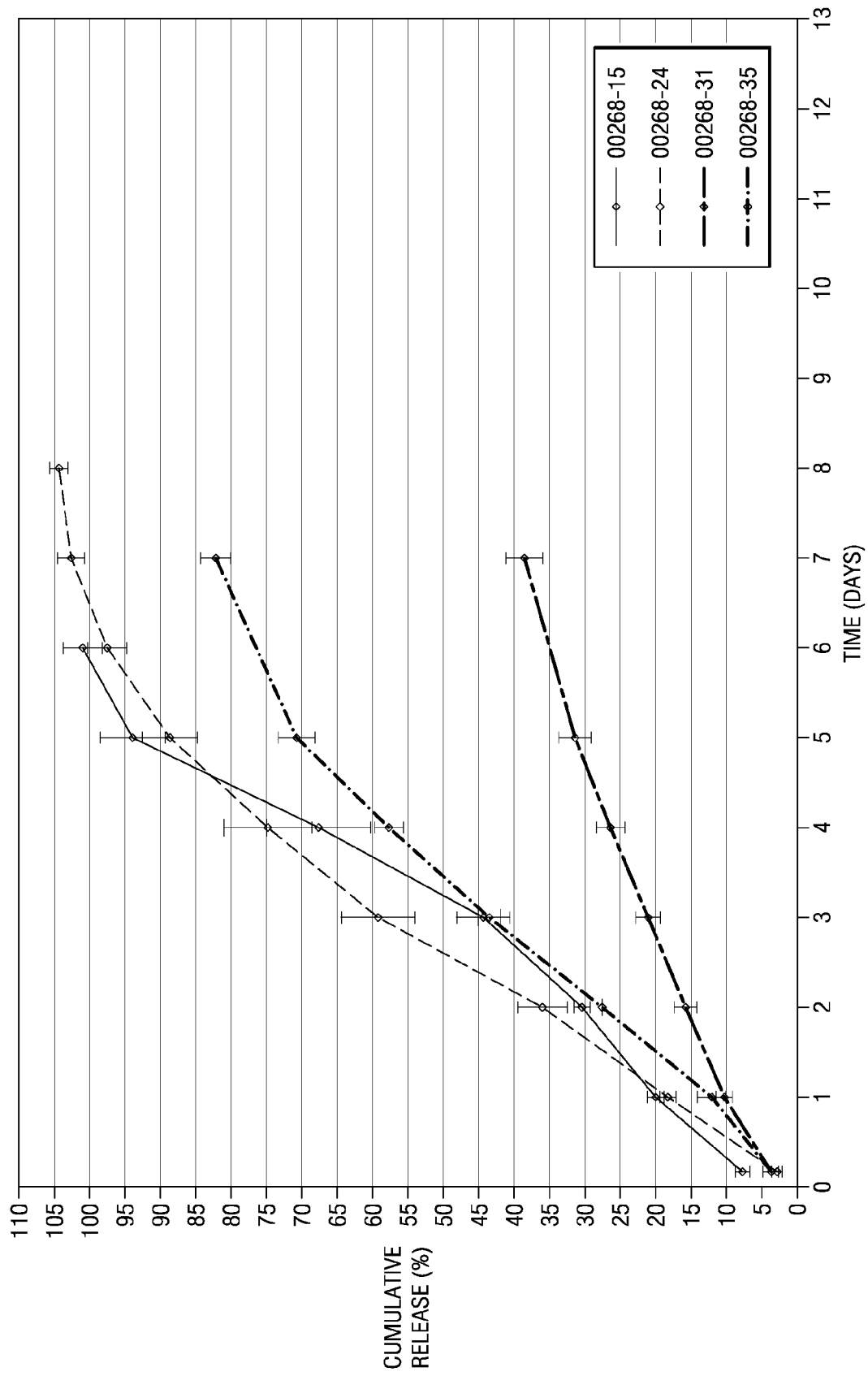
FIG. 8 is a graphic representation of the average percentage cumulative release of clonidine for certain clonidine HCl strip or ribbon implants illustrated in FIG. 6.
Figure 9:
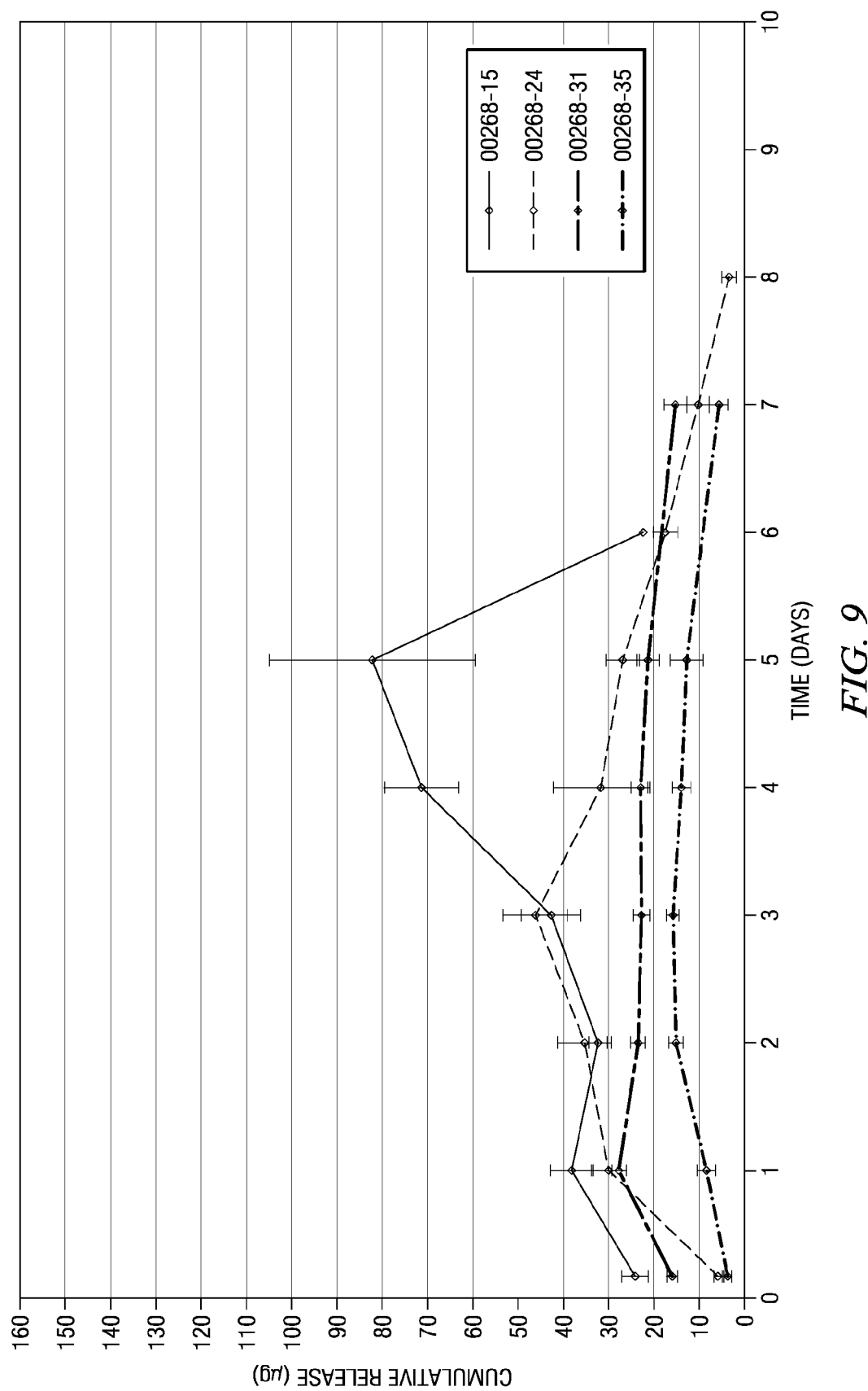
FIG. 9 is a graphic representation of the average daily release of clonidine in micrograms during days 1-8 for the certain clonidine HCl strip or ribbon implants illustrated in FIG. 8.
Figure 10:
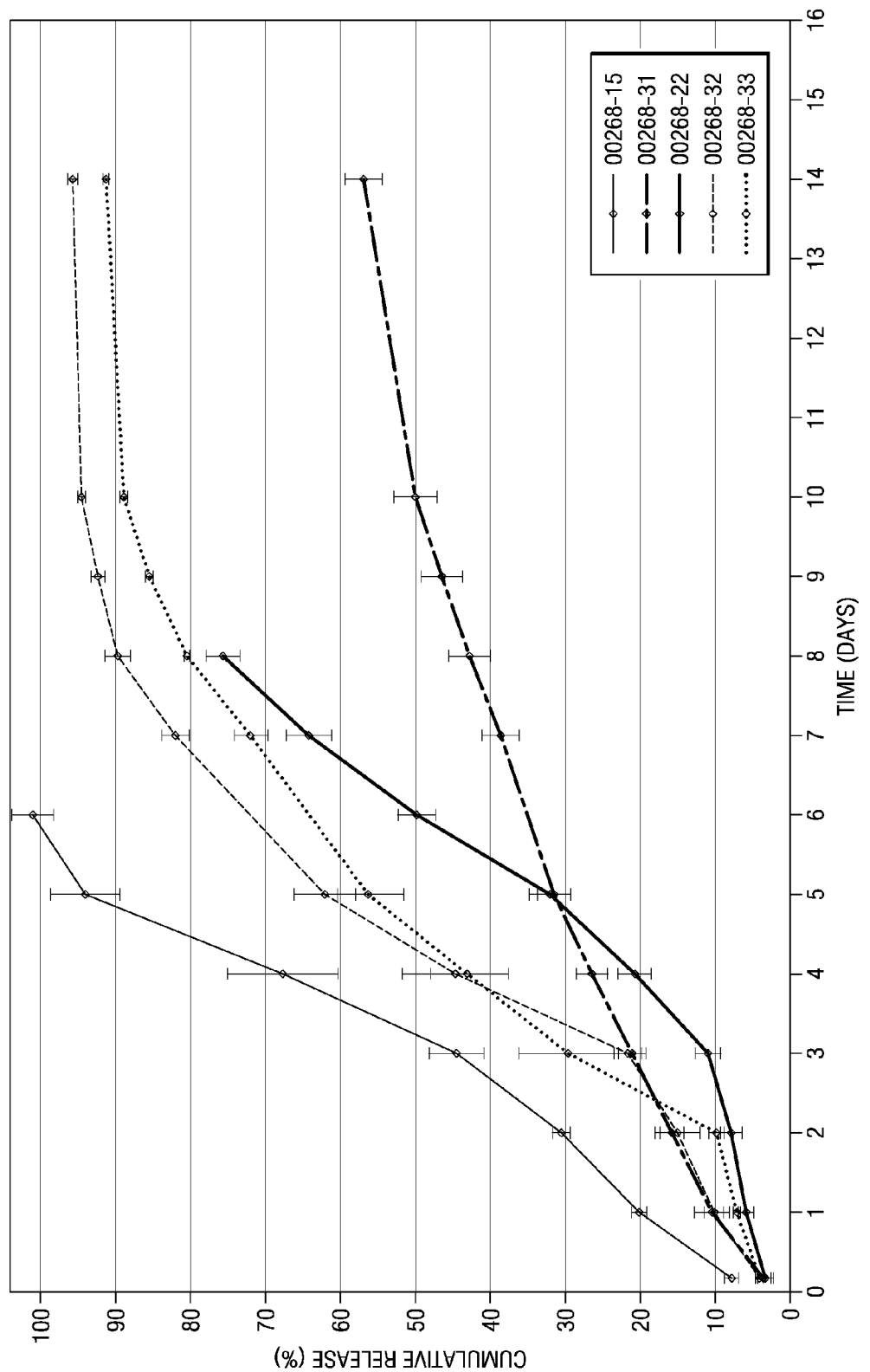
FIG. 10 is a graphic representation of the average percentage cumulative release of clonidine during days 1-14 for certain clonidine HCl strip or ribbon implants illustrated in FIG. 6.
Figure 11:
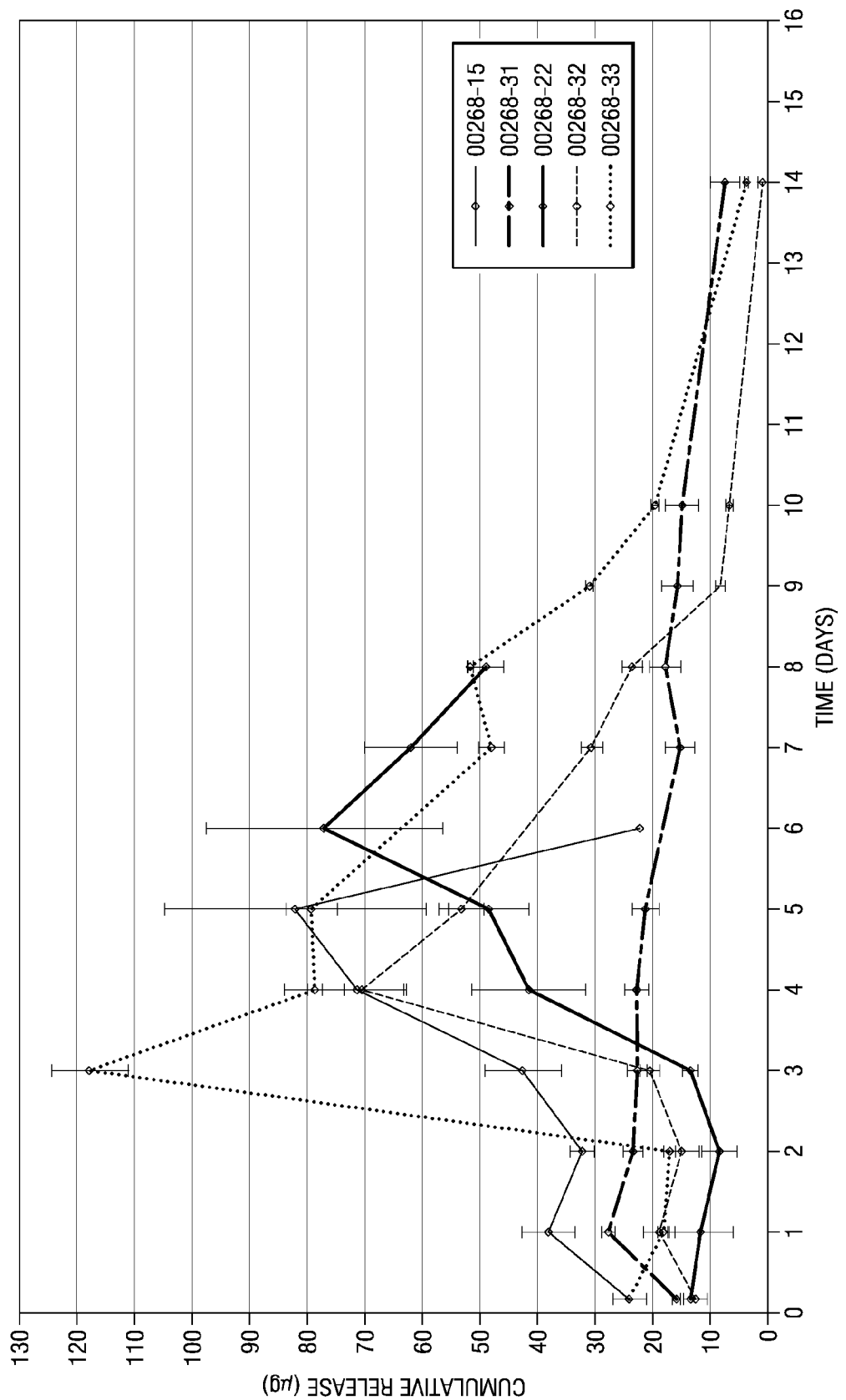
FIG. 11 is a graphic representation of the average daily release of clonidine during days 1-14 for the certain clonidine HCl strip or ribbon implants illustrated in FIG. 10.
Figure 12:
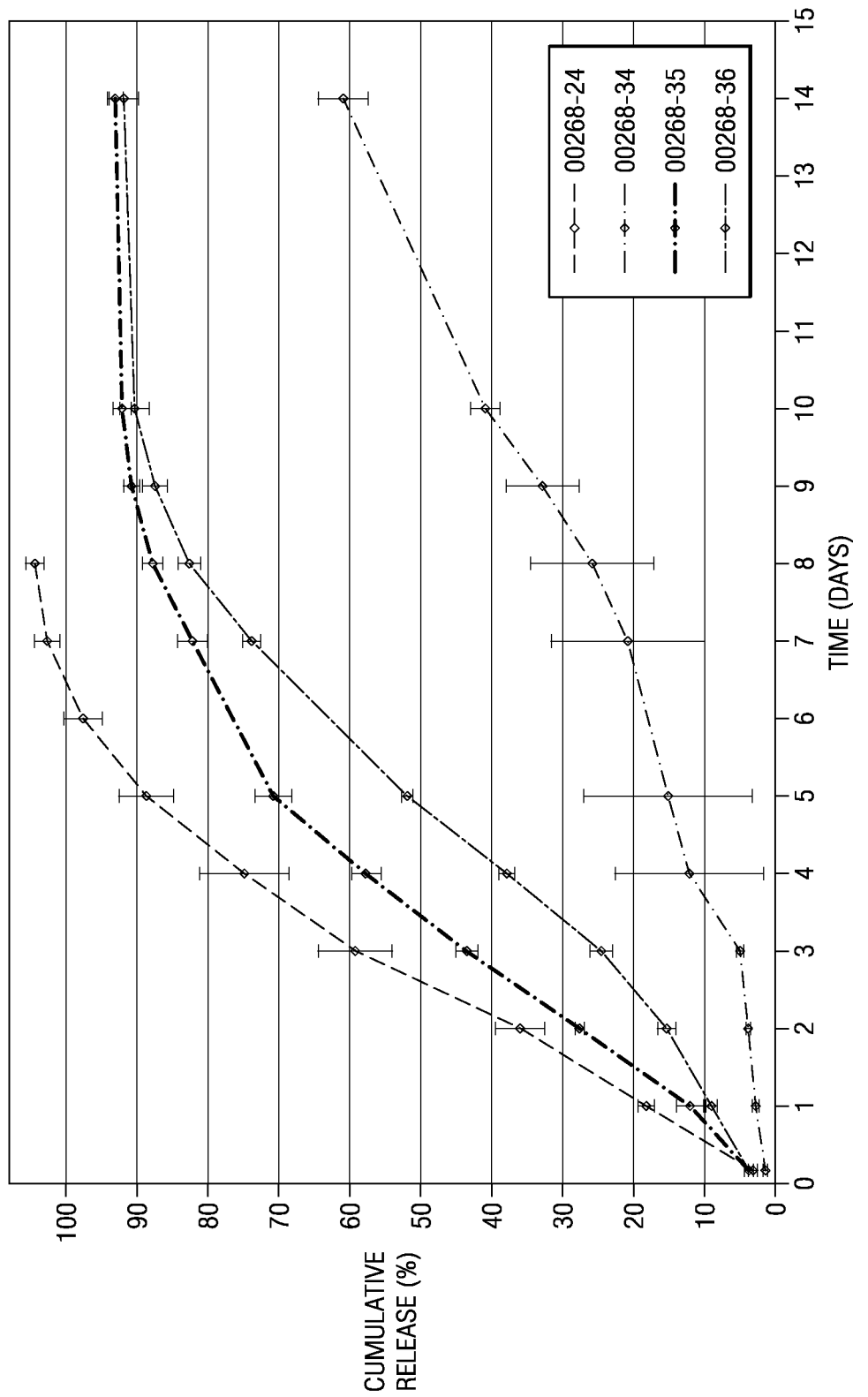
FIG. 12 is a graphic representation of the average percentage cumulative release of clonidine during days 1-14 for certain clonidine HCl strip or ribbon implants illustrated in FIG. 6.
Figure 13:
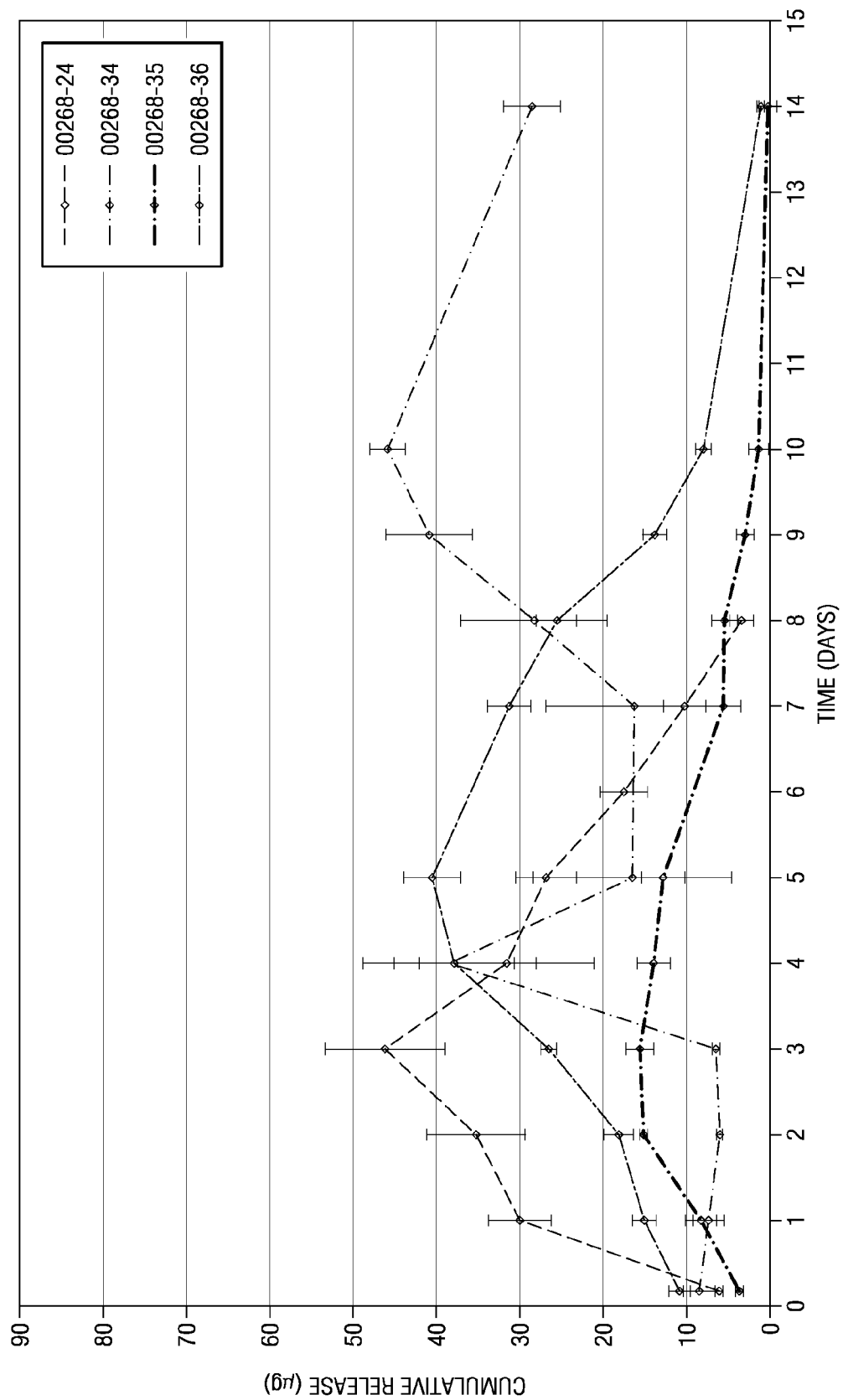
FIG. 13 is a graphic representation of the average daily release of clonidine during days 1-14 for the certain clonidine HCl strip or ribbon implants illustrated in FIG. 12.

In Vitro Drug Elution Testing: Each strip from the batch numbers from Table 2 was tested in triplicate and placed in 4 mL scintillation vials for drug elution testing. Each strip or ribbon was incubated in 2 mL of phosphate buffered saline pH 7.4 (Hyclone) at 37° C. under mild agitation. At pre-selected time points, the buffer was removed for analysis and replaced with fresh buffer medium. The drug content was quantified by HPLC. FIGS. 6 and 7 show the average release rate of clonidine in percentages and micrograms, respectively, for strips of the batch numbers from Table 2 during days 1-8. FIGS. 8 and 9 show the average release rate of clonidine in percentages and micrograms, respectively, for strips of batch numbers 00268-15, 00268-24, 00268-31 and 00268-35 from Table 2 during days 1-8. FIGS. 10 and 11 show the average release rate of clonidine in percentages and micrograms, respectively, for strips of batch numbers 00268-15, 00268-22, 00268-31, 00268-32 and 00268-33 from Table 2 during days 1-14. FIGS. 12 and 13 show the average release rate of clonidine in percentages and micrograms, respectively, for strips of batch numbers 00268-24, 00268-34, 00268-35 and 00268-36 from Table 2 during days 1-14.

The inventors were able to achieve a wide range of release profiles including some formulations with burst release initially and some formulations with linear constant release. These formulations were successful in achieving drug release for at least 14 days.

Example 3

Several clonidine HCl implants were prepared in which the drug load was varied. Representative formulations for the strip or ribbon implants are described below in Table 3. A number of tests were performed on the strip or ribbon implants including in vitro release tests in which the number of micrograms released was measured as well as the cumulative percentage release of clonidine. The results of these tests appear in FIG. 14.

Materials: Poly(D,L-lactide-co-glycolide) having a 50:50 lactide to glycolide molar ratio, a molecular weight of 8 kDa, an inherent viscosity of 0.12 dL/g and acid end capped polymer chain ends (5050 DLG 1A) was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol and acetone were also purchased from Sigma-Aldrich.

Method of Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for additional 24 hours at 70° C. and 15 mmHg vacuum.

Preparation of Melt Extruded Rods: Several formulations were prepared for melt extrusion. All of the formulations contained 5050 DLG 1A ground into powder using a Retsch (Retsch GmbH, Germany) rotor mill with an 80 micrometer sieve filter. All of the formulations contained 10% (w/w) mPEG. The rest of each of the formulations contained 5050 DLG 1A polymer and clonidine HCl with the weight percentages shown in Table 3 below. The formulations were dry mixed with a spatula prior to being feed into a Haake Mini-Lab twin screw extruder (Thermo Fischer Scientific, Waltham, Mass.). The extruder settings were as follows: 70° C. and 30 RPM for all of the formulations. All of the formulations were extruded out of a 1.5 mm diameter die.

Strip Preparation: Extruded formulations were pressed into sheets of a desired thickness using a Carver Laboratory Heat Press (Carver, Inc., Wabash, Ind.) set at 50° C. The sheets were cut by razor blades to form strip or ribbon implants of the desired dimensions for a rat paw. The dimensions of strips or ribbons made from the formulations are provided in Table 3 below.

TABLE 3

| Formulation ID | Polymer | Drug Load (%) | Excipient | Strip Size (mm) (L × W × H) |
|---|---|---|---|---|
| 13335-76-4a | 5050 DLG 1A | 5 | 10% mPEG | 9 × 1.5 × 0.5 |
| 13335-76-4d | 5050 DLG 1A | 5 | 10% mPEG | 9 × 3 × 0.25 |
| 13335-76-5a | 5050 DLG 1A | 2.5 | 10% mPEG | 9 × 3 × 0.5 |
| 13335-76-5d | 5050 DLG 1A | 2.5 | 10% mPEG | 9 × 3 × 0.25 |
| 13335-76-6 | 5050 DLG 1A | 10 | 10% mPEG | 9 × 3 × 0.25 |

Figure 14:
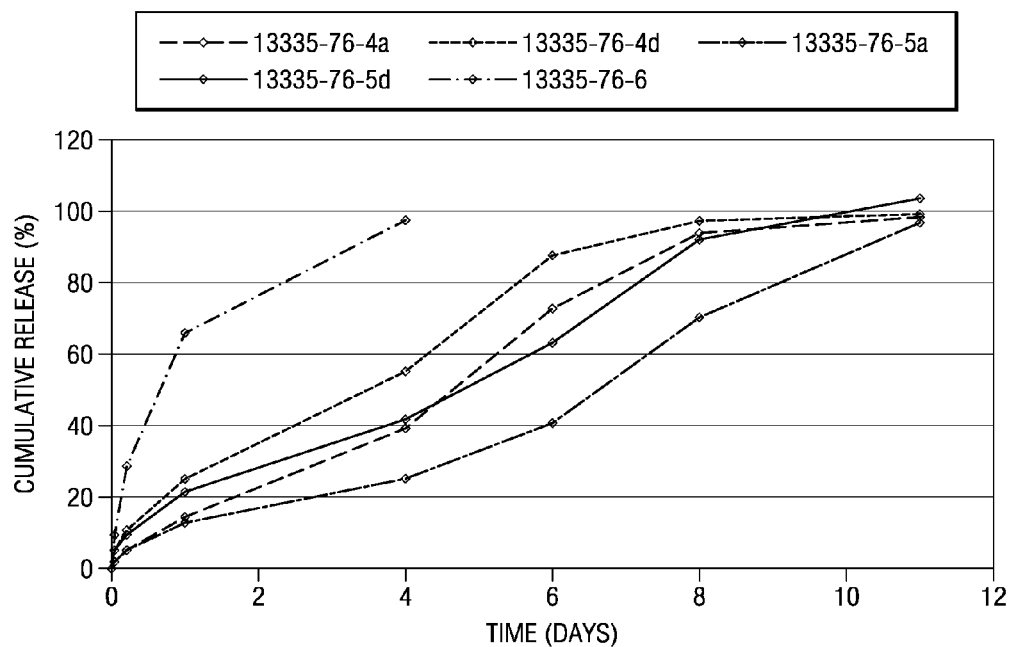
FIG. 14 is a graphic representation of the average cumulative in vitro release profile for clonidine strip implants from a study described in Example 3.

In Vitro Drug Elution Testing: Clonidine strip or ribbon implants made from the formulations from Table 3 were tested in triplicate and placed in 20 mL scintillation vials for drug elution testing. The clonidine strip or ribbon implants were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. The drug load for strips from the formulations is shown in Table 3. FIG. 14 shows the average percentage release rate of clonidine for strips from formulation ID Nos. 13335-76-4a, 13335-76-4d, 13335-76-5a, 13335-76-5d and 13335-76-6 from Table 3 during days 1-12. Clonidine formulations having an in vitro release profile for the clonidine was successfully formulated for at least 11 days. (FIG. 14).

Example 4

Figure 15:
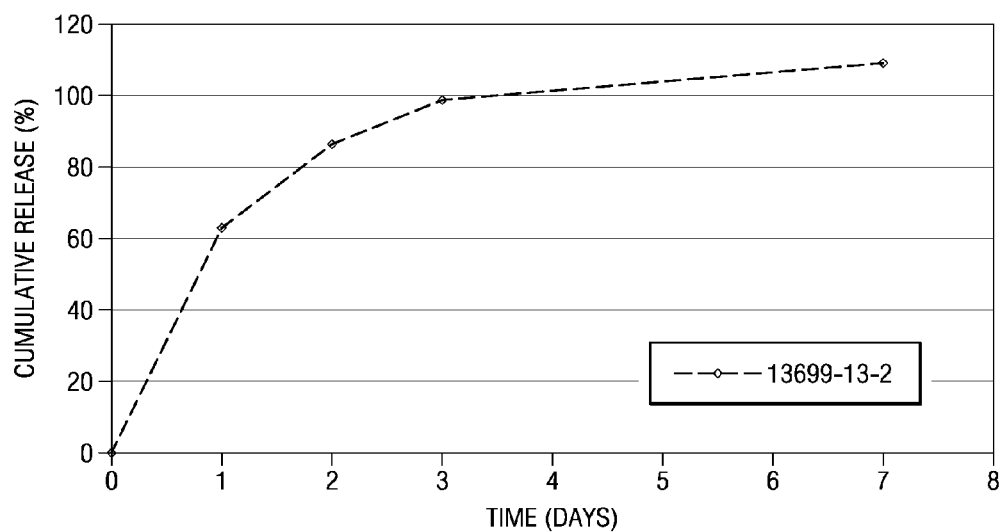
FIG. 15 shows the average cumulative in vitro release profile for clonidine strip implants from a study described in Example 4.

A clonidine HCl gel formulation was prepared. The average in vitro cumulative percentage release of clonidine was measured and is shown in FIG. 15.

Preparation of PLA Gel: Depolymerization of Polylactic Acid with Dodecanol

Polylactic acid (intrinsic viscosity of 5.71 and weight of 15.0 grams), 4-dimethylaminopyridine (weight of 9.16 grams), and dodecanol (weight of 5.59 grams) were added into a 100 mL round bottom flask, charged, capped with a rubber septum and placed in an oil bath at 140° C. The materials were heated at that temperature for 30 minutes after everything was melted and was stirred freely with a magnetic stir bar. After cooling, 15 mL of tetrahydrofuran was added into the flask to dissolve the materials and precipitated by adding heptane. After decanting off the solvents, the material was dissolved in chloroform (30 mL) and washed with hydrochloride (1 molar, 20 mL, three times) and brined once. The solution was dried over anhydrous sodium sulfate. Yellow oil was obtained after solvent removal by rota-evaporation. (Mn about 800 g/mol by end group analysis by H-NMR)

Method of Preparation of Clonidine HCl Gel Formulation: The formulation was prepared to contain 99% (w/w) PLA gel and 1% (w/w) spray-dried clonidine HCl. The two components were added to a 2 cc transfer cup and mixed in a Flacktek, Inc. Speedmixer DAC 150 FVZ for 2 minutes. The mixed formulation was then back loaded into a 1 mL BD syringe with a 18G 1.5 inch blunt tip needle.

In Vitro Drug Elution Testing: 100 uL of the gel formulation was injected in a 20 mL scintillation vial for drug elution testing. The formulation was tested in triplicate and incubated in 10 mL of phosphate buffer with 0.5% (w/w) sodium dodecyl sulfate pH 7.4 at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. The resulting formulation (Formulation ID 13699-13-2) included 1% clonidine HCL. FIG. 15 shows the average in vitro cumulative percentage release of clonidine per day for the 3 samples of the formulation that were tested.

Example 5

A clonidine HCl formulation was prepared and a number of tests were performed on strips or ribbons made from the formulation including in vitro release tests in which the number of micrograms released was measured as well as the cumulative percentage release of clonidine. The results of these tests appear in FIGS. 16-19.

Materials: Poly(D,L-lactide-co-glycolide) having a 50:50 lactide to glycolide molar ratio, a molecular weight of 8 kDa, an inherent viscosity of 0.12 dL/g and acid end capped polymer chain ends (5050 DLG 1A) was purchased from Lakeshore Biomaterials (Birmingham, Ala.). Poly(D,L-lactide-co-glycolide) having a 50:50 lactide to glycolide molar ratio, a molecular weight of 58 kDa, an inherent viscosity of 0.43 dL/g and acid end capped polymer chain ends (5050 DLG 4A) was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol was also purchased from Sigma-Aldrich.

Method of Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for an additional 24 hours at 70° C. and 15 mmHg vacuum.

Preparation of Melt Extruded Rods: The formulation containing 25 wt. % 5050 DLG 1A and 64.5 wt. % 5050DLG 4A was ground into powder using a Retsch (Retsch GmbH, Germany) rotor mill with an 80 micrometer sieve filter. The polymer powder was dry mixed with 10 wt. % mPEG with a spatula prior to being fed into a Laboratory Mixer Molder (Dynisco, Franklin, Mass.) set at 70° C. and max RPM. The polymer mixture was melt mixed for 5 minutes. Next, 0.5 wt. % spray-dried clonidine HCl was added to the polymer melt and mixed for 3 minutes in the mixer molder at 70° C. and max RPM.

Strip Preparation: The mixed formulation was pressed into sheets of a 0.5 mm thickness using a Carver Laboratory Heat Press (Carver, Inc., Wabash, Ind.) set at 50° C. The sheets were cut by razor blades to form strips/ribbons of a desired dimension. The strip implants comprising 25 wt. % 5050 DLG 1A, 64.5 wt. % 5050DLG 4A, 10 wt. % mPEG and 0.5% spray-dried clonidine HCl were then tested for their in vitro release.

In Vitro Drug Elution Testing: Three clonidine strip implants prepared according to the procedure described in this example having the dimensions 20 mm×5 mm×0.5 mm were placed in 20 mL scintillation vials for drug elution testing. The clonidine strips were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader.

Figure 16:
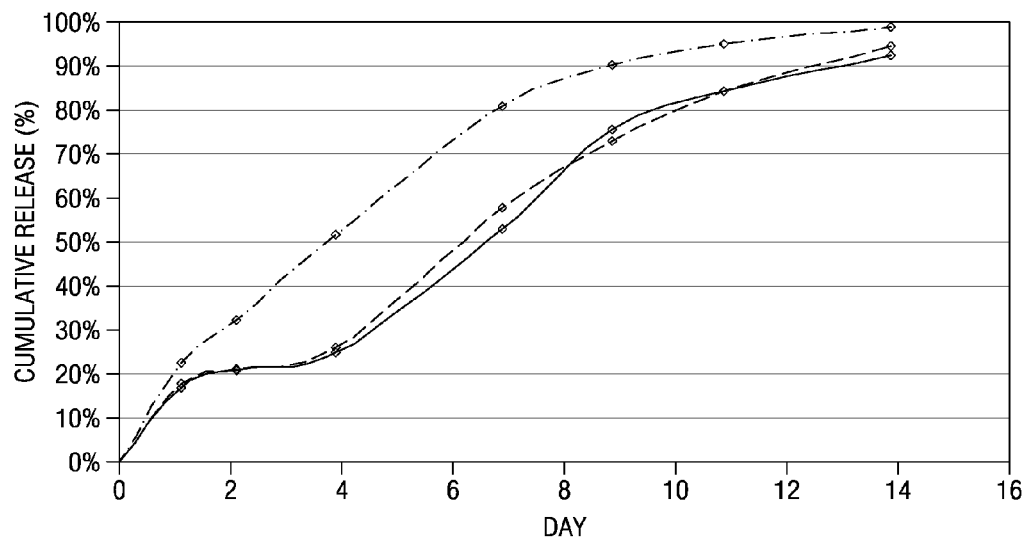
FIG. 16 is a graphic representation of the percentage cumulative release of clonidine for three clonidine strip implants from a study described in Example 5.
Figure 17:
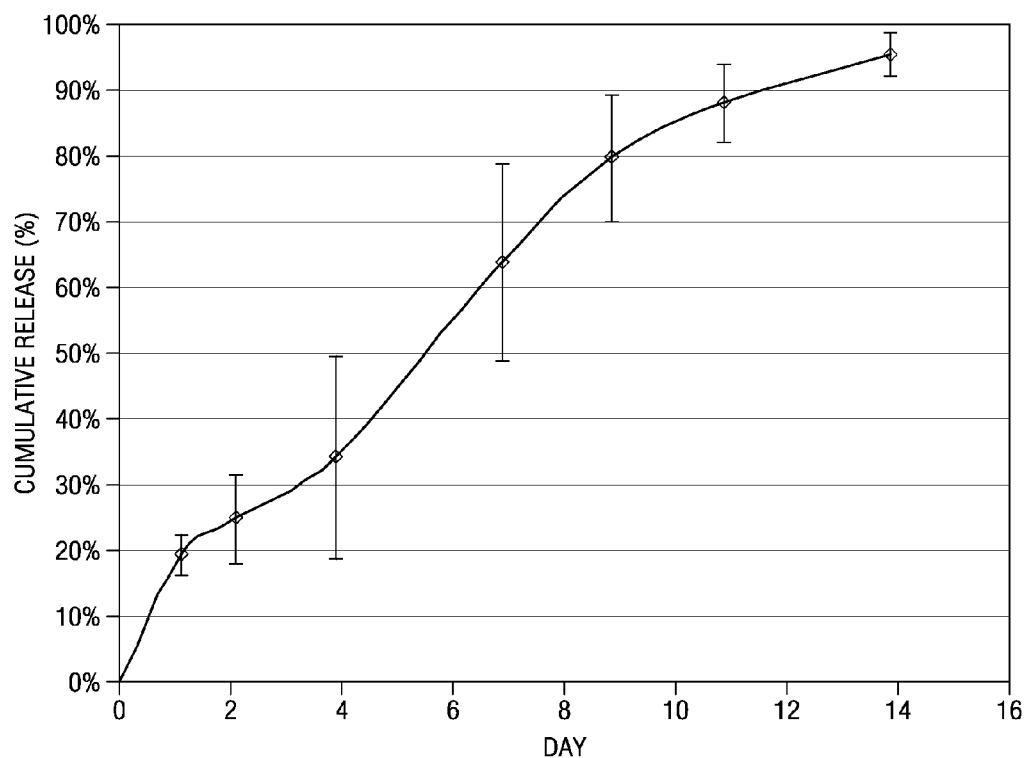
FIG. 17 is a graphic representation of the average percentage cumulative release of clonidine for the clonidine strip implants shown in FIG. 16.

FIGS. 16 and 17 are in vitro graphic representations of the percentage cumulative release of three sterilized clonidine strip implants. As is readily apparent in these figures, each strip released between 90% and 100% of the clonidine over 14 days with an average of 5%-10% of drug released every day. The average cumulative drug release of the three strips is shown in FIG. 17, where 95% of the drug released in 14 days.

Figure 18:
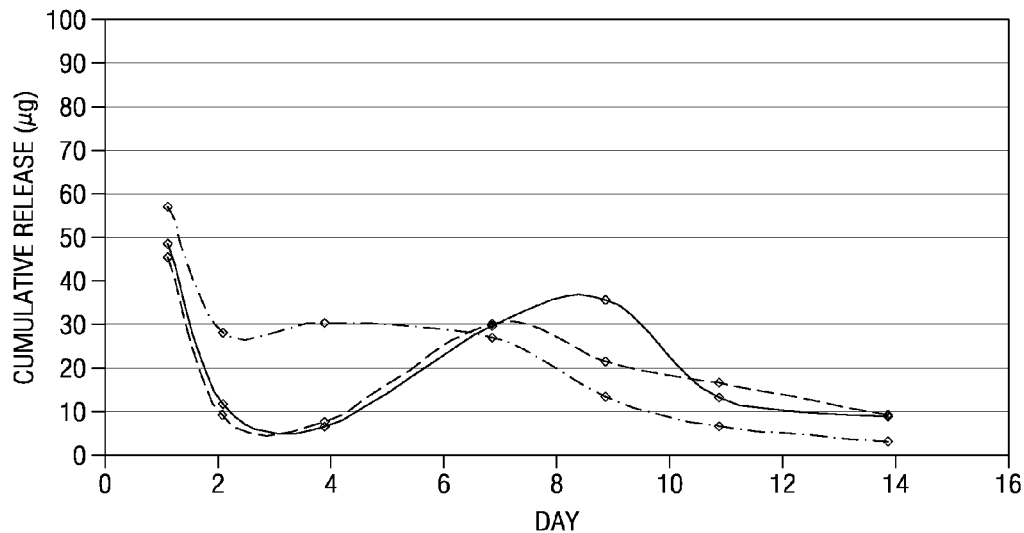
FIG. 18 is a graphic representation of the cumulative in vitro release of clonidine in ug for the three clonidine strip implants described in Example 5.
Figure 19:
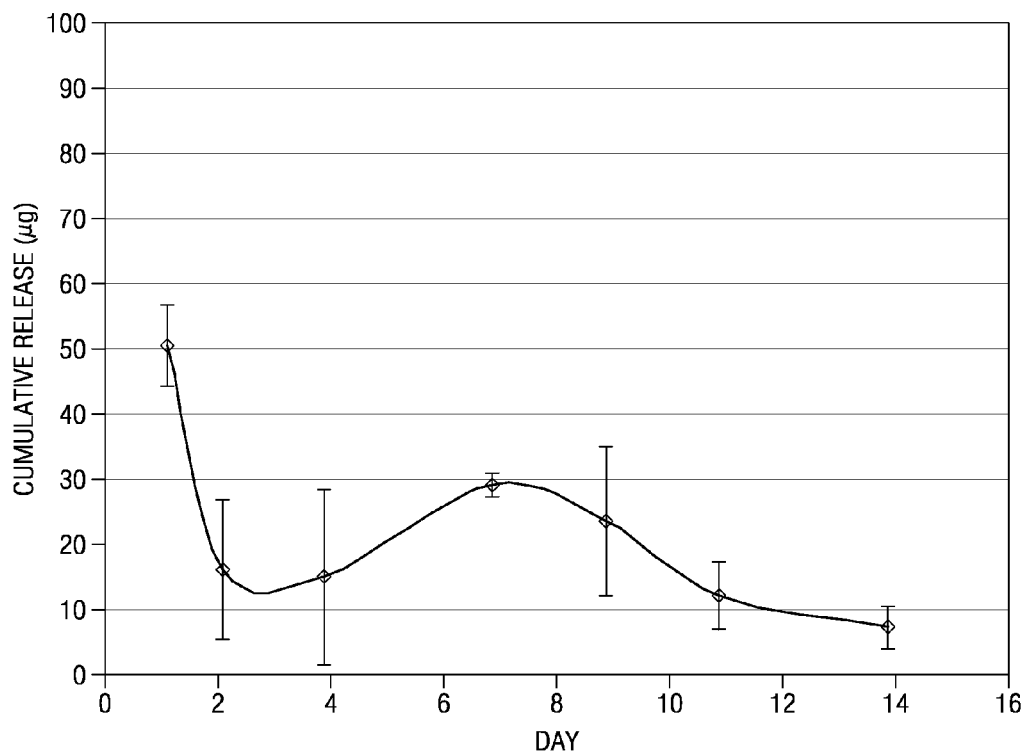
FIG. 19 is a graphic representation of the average cumulative in vitro release of clonidine in ug for the clonidine strip implants shown in FIG. 18.

FIGS. 18 and 19 are in vitro graphic representations of the daily release profile of the three sterilized clonidine strip implants and their cumulative average daily release in micrograms per day. As is readily apparent in these figures, each drug depot had an initial burst effect with a release of clonidine HCl at a dose of about 45 to 60 mcg within about 1 day. After the first day, each drug depot released about 5-35 mcg per day until the drug depot was exhausted at day 14.

Example 6

In vivo Efficacy Evaluation of Clonidine Implants in the Pig Surgical Model

Induction of Post-Operative Pain in Piglets: Piglets were anesthetized by an Isoflurane/Oxygen mixture, which was delivered through a face mask. A 5 cm long skin and fascia incision was made to the right femur at the groin keeping the muscle intact. The skin incision was closed with metal clamps. The duration of the anesthesia was less than 10 minutes. Immediately after the incision, the animals were administered with either control or drug implants into the incisional space. Morphine (Mor) was administered subcutaneously in the animals in a morphine group as a positive control.

Analgesia Evaluation: The analgesic effect of the clonidine implants was assessed using pain behavior scoring. The pain scoring system was the summation of 3 major categories:
1. Animal solitary performance (walking and vocalization)
2. Animal social behavior
3. The length of time in which the pigs stayed on a sling All animals were observed at baseline (3 days prior to surgery) and at 1 and 3 hours post surgery (study day 0). Pain behavior was then assessed daily for 4 more days (study days 1, 2, 3 and 4). The implants were administered into the surgical wound bed on study day 0 immediately right after surgery. Morphine was administered one hour prior to pain assessment in animals in the morphine group (Mor).

Figure 20:
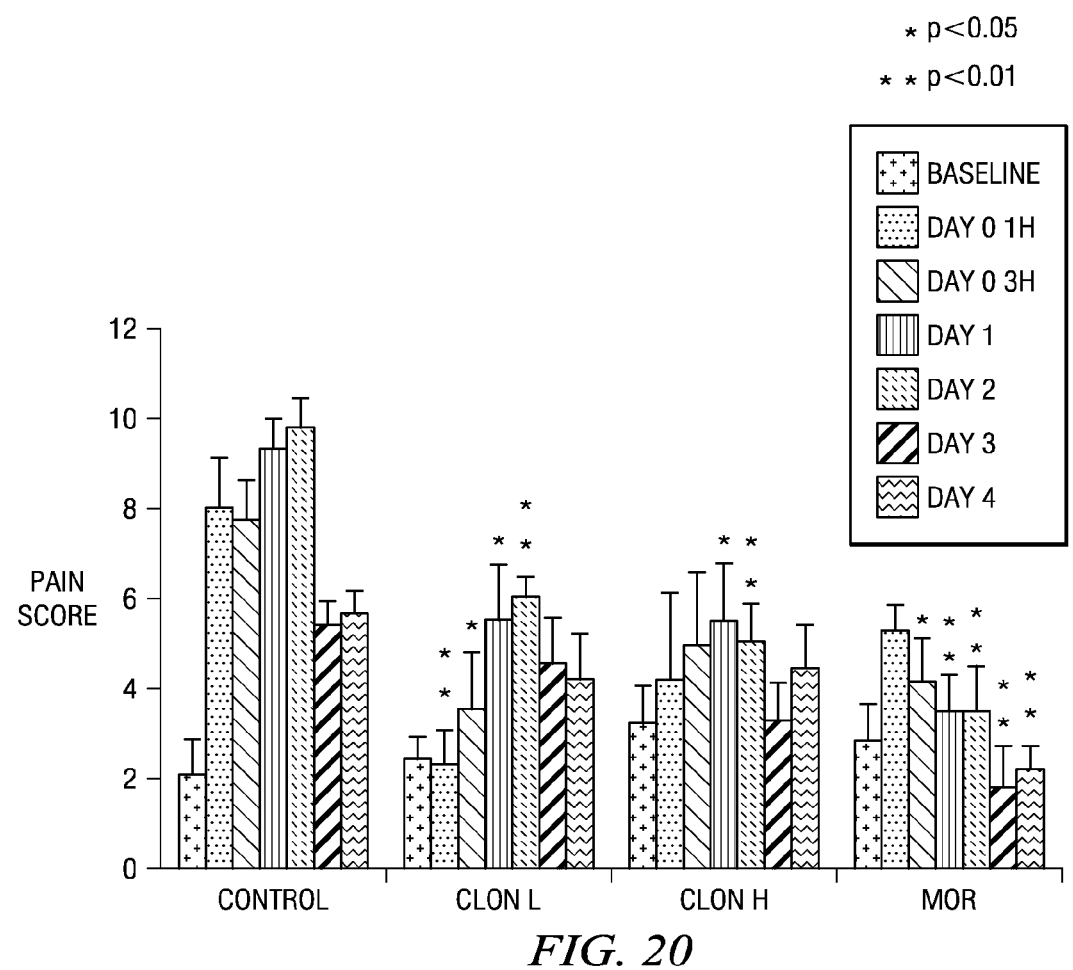
FIG. 20 is a graphic representation of pain scores of clonidine depots implanted post-operatively at the surgical incision.

Results: FIG. 20 shows an in vivo efficacy evaluation of clonidine high dose (1500 mcg loaded in the depot, designed to release 150 mcg/day) implants and clonidine low dose (750 mcg loaded in the depot, designed to release 75 mcg/day) implants as measured by pain scores at 0 hours (baseline), 1 hour, 3 hours, day 1, day 2, day 3 and day 4, post-treatment. Pigs receiving the clonidine low dose implant exhibited significantly reduced pain scores on day 0 at 1 hour and 3 hours post-treatment and on days 1 and 2 post-treatment compared to pigs receiving the control polymer. The effect of the low dose clonidine implant at days 3 and 4 could not be determined as the post-operative pain in this model dissipated around day 3 or day 4. The low dose clonidine implant showed statistically significant reduction in pain on days 1 and 2 compared to the control polymer. FIG. 20 also shows the effect of morphine at all tested time points.

Pigs receiving the clonidine high dose implant exhibited significantly reduced pain scores on day 0 at 1 hour and 3 hours post-treatment and on days 1 and 2 compared to pigs receiving the control polymer. It is also readily apparent from FIG. 20 that the pain score was reduced at all time points for pigs receiving the clonidine high dose implant compared to the control polymer.

Conclusion: In view of the findings obtained under the conditions of this study, treatment with clonidine high dose and low dose implants was effective in reducing post-operative pain in pigs.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for reducing or treating post-operative pain in a patient in need of such treatment, the implantable drug depot comprising a therapeutically effective amount of clonidine or pharmaceutically acceptable salt thereof and a polymer comprising poly(D,L-lactide-co-caprolactone) or poly(L-lactide-co-caprolactone) or a combination thereof; wherein the depot is implantable at a site beneath the skin to reduce or treat post-operative pain, and the depot is capable of releasing (i) about 5% to about 45% of the clonidine or pharmaceutically acceptable salt thereof relative to a total amount of the clonidine or pharmaceutically acceptable salt thereof loaded in the drug depot over a first period of up to 48 hours and (ii) about 55% to about 95% of the clonidine or pharmaceutically acceptable salt thereof relative to a total amount of the clonidine or pharmaceutically acceptable salt thereof loaded in the drug depot over a subsequent period of at least 3 days, and the polymer comprises an inherent viscosity from about 0.10 dL/g to about 1.2 dL/g.

2. An implantable drug depot according to claim 1, wherein the clonidine is in the form of a hydrochloric salt.

3. An implantable drug depot according to claim 1, wherein the polymer comprises one or more of poly(lactide-co-glycolide), polylactide, polyglycolide, polyorthoester, D-lactide, D,L-lactide, poly(D,L-lactide), L-lactide, poly(D,L-lactide-co-glycolide-co-caprolactone), polycaprolactone or a combination thereof.

4. An implantable drug depot according to claim 1, wherein the polymer comprises about 60% to about 90% of the total wt. % of the drug depot.

5. An implantable drug depot according to claim 1, wherein the polymer is capable of degrading in 30 days or less after the drug depot is implanted at the site.

6. An implantable drug depot according to claim 1, wherein the clonidine is released in an amount between 0.05 ug and 3 mg per day for a period of 3 to 10 days.

7. An implantable drug depot according to claim 1, wherein the clonidine is present in an amount of about 0.1 to about 10 wt. % of the implantable drug depot and the polymer is present in an amount of about 75 to about 94 wt. % of the implantable drug depot, and the drug depot further comprises from about 5 to about 15 wt. % of an excipient.

8. An implantable drug depot according to claim 1, wherein the clonidine is present in an amount of about 0.1 to about 10 wt. % of the implantable drug depot and the polymer comprises PLGA in an amount of about 75 to about 94 wt. % of the depot, and the depot further comprises from about 5 to about 15 wt. % mPEG.

9. A method of making an implantable drug depot of claim 1, the method comprising combining a biocompatible polymer and a therapeutically effective amount of the clonidine or pharmaceutically acceptable salt thereof and forming the implantable drug depot from the combination.

10. A method of treating post-operative pain in a patient in need of such treatment, the method comprising delivering one or more biodegradable drug depots comprising a polymer; and a therapeutically effective amount of clonidine or pharmaceutically acceptable salt thereof to a target tissue site beneath the skin before, during or after surgery, wherein the drug depot is capable of releasing an initial bolus dose of the clonidine or pharmaceutically acceptable salt thereof at a site beneath the skin followed by a sustained release dose of an effective amount of the clonidine or pharmaceutically acceptable salt thereof over a period of at least 3 days, and the polymer comprises an inherent viscosity from about 0.45 dL/g to about 1.0 dL/g.

11. A method of treating post-operative pain according to claim 10, wherein the drug depot releases about 55% to about 85% of the clonidine or pharmaceutically acceptable salt thereof relative to a total amount of the clonidine loaded in the drug depot over a period of 3 to 10 days after the drug depot is administered to the target tissue site.

12. A method of treating post-operative pain according to claim 10, wherein the drug depot releases between 0.05 ug and 3 mg/day of the clonidine or pharmaceutically acceptable salt thereof for a period of 4 to 10 days.

13. A method of treating post-operative pain according to claim 10, wherein the polymer comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

14. A method of treating post-operative pain according to claim 10, wherein the polymer comprises about 60% to about 90% of the total wt. % of the drug depot.

15. An implantable drug depot comprising: (i) a therapeutically effective amount of clonidine or pharmaceutically acceptable salt thereof; and (ii) a polymer;
wherein the drug depot is capable of releasing an initial bolus dose of clonidine or pharmaceutically acceptable salt thereof at a site beneath the skin, and the drug depot is capable of releasing a sustained release dose of an effective amount of clonidine or pharmaceutically acceptable salt thereof over a subsequent period of 3 to 10 days; and
wherein the polymer comprises poly(D,L-lactide-co-caprolactone) or poly(L-lactide-co- caprolactone) or a combination thereof, and the polymer comprises an inherent viscosity from about 0.45 dL/g to about 1.0 dL/g.

16. An implantable drug depot according to claim 15, wherein the drug depot releases about 55% to about 85% of the clonidine or pharmaceutically acceptable salt thereof relative to a total amount of clonidine loaded in the drug depot over the subsequent period of 3 to 10 days after the drug depot is administered.

17. An implantable drug depot according to claim 15 wherein the drug depot releases between 0.05 ug and 3 mg/day of clonidine or pharmaceutically acceptable salt thereof.

18. An implantable drug depot according to claim 15, wherein the polymer comprises about 60% to about 90% of the total wt. % of the drug depot.

19. An implantable drug depot according to claim 15, wherein the clonidine is in the form of a hydrochloric salt.

20. An implantable drug depot according to claim 15, wherein the initial bolus dose of the clonidine is about 15% to about 45% of the clonidine or pharmaceutically acceptable salt thereof relative to a total amount of clonidine loaded in the drug depot.

21. An implantable drug depot according to claim 1, wherein the depot is in the form of a strip.

* * * * *

UNITED STATES PATENT AND TRADEMARK OFFICE
CERTIFICATE OF CORRECTION

PATENT NO. : 9,211,285 B2
APPLICATION NO. : 14/097983
DATED : December 15, 2015
INVENTOR(S) : McKay et al.

Page 1 of 1

It is certified that error appears in the above-identified patent and that said Letters Patent is hereby corrected as shown below:

Specification

In Column 1, Lines 5-6, delete "of co-pending" and insert -- of --, therefor.

In Column 1, Line 7, delete "2009" and insert -- 2009, now Pat. No. 8,629,172, --, therefor.

In Column 1, Line 13, delete "in" and insert -- into --, therefor.

In Column 9, Line 66, delete "papavereturn," and insert -- papaveretum, --, therefor.

In Column 10, Line 40, delete "then" and insert -- than --, therefor.

In Column 21, Line 20, delete "inflammed" and insert -- inflamed --, therefor.

Signed and Sealed this
Tenth Day of May, 2016

Michelle K. Lee
*Director of the United States Patent and Trademark Office*